(12) United States Patent
Durica et al.

(10) Patent No.: US 12,694,958 B2
(45) Date of Patent: Jul. 28, 2026

(54) PLATFORM SUPPORTING CENTRALIZED ACCESS FOR REMOTE MRI WORKFLOW FOR IMPLANTED DEVICES

(71) Applicant: Pacesetter, Inc., Sylmar, CA (US)

(72) Inventors: Amber Durica, San Francisco, CA (US); Yash Vardhan Tiwari, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 182 days.

(21) Appl. No.: 18/482,388

(22) Filed: Oct. 6, 2023

(65) Prior Publication Data

US 2024/0203550 A1    Jun. 20, 2024

Related U.S. Application Data

(60) Provisional application No. 63/432,457, filed on Dec. 14, 2022.

(51) Int. Cl.
*G16H 10/65*          (2018.01)
*G16H 40/40*          (2018.01)

(52) U.S. Cl.
CPC .............. *G16H 10/65* (2018.01); *G16H 40/40* (2018.01)

(58) Field of Classification Search
CPC .... A61N 1/37512; A61B 5/686; A61B 5/055; G16H 10/60; G16H 40/60
See application file for complete search history.

(56) References Cited

U.S. PATENT DOCUMENTS

| | | | |
|---|---|---|---|
| 8,521,304 | B2 | 8/2013 | Chen et al. |
| 8,538,553 | B2 | 9/2013 | Zhao et al. |
| 8,554,338 | B2 | 10/2013 | Doan et al. |
| 8,600,520 | B2 | 12/2013 | Doan et al. |
| 9,211,406 | B2 | 12/2015 | Bornzin et al. |
| 9,293,818 | B2 | 3/2016 | Min |

(Continued)

OTHER PUBLICATIONS

Sheeba J. Sujit, Eliana Bonfante, Azin Aein, Ivan Coronado, Roy Riascos-Castaneda, Luca Giancardo, Deep learning enabled brain shunt valve identification using mobile phones, Computer Methods and Programs in Biomedicine, vol. 210, 2021 (Year: 2021).*

(Continued)

*Primary Examiner* — Joseph D Burgess
(74) *Attorney, Agent, or Firm* — Christopher R. Carroll; Carroll, Hoette & Butscher, LLC

(57)          ABSTRACT

A healthcare system comprises an MR platform comprising non-transitory memory storing program instructions and patient specific records that include information associated with an implantable medical device (IMD) and a patient. The MR platform has processors that, when executing the program instructions, are configured to i) receive an MRI exam referral requesting an MRI exam associated with a first patient specific record from within the patient specific records that has a first IMD and a first patient; ii) responsive to the MRI exam referral, automatically transmit an MRI exam request alert; iii) responsive to receiving a response to the MRI exam request alert, provide access to the first patient specific record; iv) receive MRI settings associated with the first patient specific record that are configured to be programmed into the first IMD in advance of the MRI exam; and v) store the MRI settings in the patient specific record.

15 Claims, 9 Drawing Sheets

(56)     References Cited

U.S. PATENT DOCUMENTS

| 2011/0144722 | A1  | 6/2011  | Min et al. |
| 2012/0101544 | A1* | 4/2012  | Hoberman ......... A61N 1/37254 |
|              |     |         | 607/30 |
| 2013/0053920 | A1* | 2/2013  | LaLonde .............. A61N 1/3718 |
|              |     |         | 607/30 |
| 2014/0163892 | A1* | 6/2014  | von Arx ............... G01R 33/288 |
|              |     |         | 702/19 |
| 2016/0038744 | A1* | 2/2016  | Ellingson ............. A61N 1/3718 |
|              |     |         | 607/17 |
| 2017/0348537 | A1* | 12/2017 | Gadagkar .......... A61N 1/37264 |
| 2018/0140856 | A1  | 5/2018  | Lindevig et al. |
| 2018/0344198 | A1* | 12/2018 | Gebhardt .............. A61B 5/055 |
| 2019/0224475 | A1  | 7/2019  | Dubuclet |
| 2021/0127976 | A1* | 5/2021  | Starobinets .......... A61B 5/0033 |
| 2021/0187284 | A1  | 6/2021  | Dubuclet |
| 2022/0338809 | A1  | 10/2022 | Sison et al. |
| 2022/0339452 | A1  | 10/2022 | Sison et al. |
| 2023/0054317 | A1  | 2/2023  | Skup et al. |
| 2023/0061204 | A1* | 3/2023  | Edmonson ......... A61N 1/37223 |

OTHER PUBLICATIONS

U.S. Appl. No. 18/337,282 filed Jun. 19, 2023 (84 pages).
IMV "Benchmark Report" MR 2019 (26 pages).

* cited by examiner

220

PATIENT SPECIFIC RECORD

250
Identifying information

260
Remote programming

252
Summary of implanted system

262
MRI settings

254
Implant history

264
Operational settings

256
MR conditions of use

266
Physician's order

258
MRI history

268
Smart MRI settings

Receive MRI exam referral ~402

Transmit MRI exam request alert ~404

Access patient specific record via MRI implant portal ~406

Review remote programming status and MRI pre-checks ~408

Transmit MRI information request alert ~410

Save MRI settings in patient specific record ~412

Transmit MRI scheduling request alert ~414

PLATFORM SUPPORTING CENTRALIZED ACCESS FOR REMOTE MRI WORKFLOW FOR IMPLANTED DEVICES

CROSS-REFERENCE TO RELATED APPLICATIONS

This application claims priority to U.S. Provisional Patent Application No. 63/432,457, filed 14 Dec. 2022, entitled "PLATFORM SUPPORTING CENTRALIZED ACCESS FOR REMOTE MRI WORKFLOW FOR IMPLANTED DEVICES", the subject matter of which is incorporated herein by reference in its entirety.

BACKGROUND

Embodiments of the present disclosure generally concern methods and systems related to centralizing access to information that is needed to accomplish magnetic resonance imaging workflow associated with scanning patients who have implanted devices, such as active implanted devices and/or MR conditional implanted devices.

Magnetic resonance imaging (MRI) is an effective, non-invasive imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnet that generates a powerful static magnetic field. The static magnetic field causes protons within tissues of the body to align with an axis of the static field. A pulsed radio-frequency (RF) magnetic field is then applied causing precession of the protons around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

A significant problem with MRI is that its strong magnetic fields can interfere with the operation of implantable medical devices (IMDs), such as a pacemaker, cardiac resynchronization therapy (CRT) device, implantable cardioverter defibrillator device (ICD), neurostimulation (NS) device, implantable cardiac monitor (ICM), leadless IMD and other electronic devices implanted within the patient. Typically, IMDs that deliver therapy include pulse generators for generating electrical pacing pulses and shocking circuits for generating stronger defibrillation shocks. The IMD may include one or more electrodes located on the housing of the device and/or include one or more electrodes located on lead(s) that are coupled to the IMD. The IMD and/or lead may be configured to be implanted subcutaneously, trans-venous proximate the spine, within the skull and the like. IMDs are configured to collect various types of biological signals, analyze the biological signals for various conditions, in some cases communicate the biological signals and/or conditions to an external device, and/or deliver therapy. The therapy may include delivering pacing pulses, delivering defibrillation shocks, delivering neurostimulation pulses, releasing a drug, transmitting a notification and the like.

The leads, and/or the IMD itself, may also have a variety of sensors for sensing physiological signals within the heart of the patient, such as electrical sensors, pressure sensors, temperature sensors, $SvO_2$ sensors, photoplethysmography (PPG) and the like. The sensors are typically connected to the implantable device via electrical signal conduction paths within the various leads so as to receive control signals from the implanted device and to relay sensed signals back to the device.

With conventional implantable systems, the strong MRI fields can prevent the implanted device from reliably sensing signals from the various electrodes of the leads and from the various physiological sensors, resulting in improper and/or dangerous operation. Therefore, some MR conditional implants are placed in an MRI mode and/or programmed with MRI settings that may temporarily limit, or disable, the IMD's normal device operation and intended therapy delivery. For example, a pacemaker may be programmed to a predetermined pacing setting and native/inherent signal detection is discontinued prior to the MRI exam. After the MRI exam is complete, the previous settings of the device have to be restored, and the proper operation of the device and health of the patient have to be verified. While the MRI settings of some devices can be set by the patient, many devices require personnel such as IMD clinic staff or implant manufacturer staff of the manufacturer to program the device into MRI mode and then return the device to normal operation. In many situations, personnel with expertise in the IMD(s) need to be on-site at the MRI clinic to accomplish this task.

To address these concerns, certain procedures must be followed to ensure the safety of the patient during the MRI exam as well as after the MRI exam is completed. Currently, participants in the scheduling and scanning processes can include the patient, the referring physician/clinic staff, staff of the MRI clinic, staff of the implant clinic, and the implant manufacturer's staff (e.g., field staff or field representatives, technical support services), etc., all of whom coordinate care in-person, and through phone calls and fax. Accordingly, a significant burden is placed on all participants.

Further, patients with implanted medical devices are provided with one or more physical card(s), approximately the size of a credit card, that contains information related to their implant(s). The patient should present this card to their health care providers, such as when they are preparing for and having an MRI exam, so that the provider has the appropriate information. However, adherence to carrying the card is low and it is not guaranteed that the card will be updated as changes to the implant(s) occur.

Accordingly, there is a need to provide improved work-flow systems for MRI scanning of patients who have implanted devices that ensure the safety of the patient while decreasing the burden on each of the participants.

SUMMARY

In accordance with embodiments herein, a healthcare system comprises a magnetic resonance (MR) platform comprising non-transitory memory configured to store program instructions and patient specific records associated with individual patients. Each of the patient specific records includes information associated with an implantable medical device (IMD) and a patient. The MR platform further comprises one or more processors that, when executing the program instructions, are configured to i) receive a magnetic resonance imaging (MRI) exam referral requesting an MRI exam associated with a first patient specific record from within the patient specific records, the first patient specific record having an associated first IMD and a first patient; ii) responsive to the MRI exam referral, automatically transmit an MRI exam request alert; iii) responsive to receiving a response to the MRI exam request alert, provide, via a graphical user interface, access to the first patient specific record; iv) receive MRI settings associated with the first patient specific record, the MRI settings configured to be programmed into the first IMD in advance of the MRI exam; and v) responsive to receiving the MRI settings, store the MRI settings in the patient specific record.

Optionally, the MR platform is configured to integrate with i) an existing device platform, ii) a patient application, iii) a third-party healthcare management system, or iv) a device-based health kit. Optionally, wherein responsive to the MRI exam referral, the one or more processors are further configured to automatically generate a ticket associated with the first patient. Optionally, the one or more processors are further configured to receive a query.

Optionally, the memory is further configured to store MRI conditions of use associated with a plurality of IMDs or links to the MRI conditions of use associated with the plurality of IMDs. Optionally, the memory is further configured to store adverse reports associated with a plurality of IMDs or links to the adverse reports associated with the plurality of IMDs. Optionally, the memory is further configured to store a centralized ledger including data associated with a plurality of patients. Optionally, the memory is further configured to store MRI history associated with the first patient specific record. The MRI history includes information associated with one or more previous MRI exams of the first patient. Optionally, the information associated with the one or more previous MRI exams includes i) MR scanner information, ii) MRI scan parameters, or iii) scan regions associated with the one or more previous MRI exams.

Optionally, the one or more processors are further configured to, responsive to receiving the MRI exam referral, automatically transmit an MRI scheduling request alert to i) IMD programming personnel, ii) a field representative, iii) the first patient, iv) an MRI clinic, v) a physician's office, or vi) an implant clinic. Optionally, the one or more processors are further configured to, in response to receiving a response to the MRI scheduling request alert, provide controlled access to the first patient specific record. The level of control is based on a respondent to the MRI scheduling request alert, and the controlled access includes displaying information accessible to the respondent.

Optionally, the one or more processors are further configured to, in response to receiving a response to the MRI scheduling request alert, provide controlled access to the first patient specific record, wherein the level of control is based on a respondent to the MRI scheduling request alert, wherein the controlled access includes displaying information accessible to the respondent. Optionally, the one or more processors are further configured to i) responsive to receiving the MRI exam referral, automatically transmit an MRI scheduling request alert, and ii) responsive to receiving a response to the MRI scheduling request alert, display scheduling data associated with the MRI exam request via a portal.

Optionally, the one or more processors are further configured to determine Smart MRI settings for programming the first IMD associated with the first patient during an MRI exam. The Smart MRI settings are based on information associated with i) previous MRI exams of the first patient, ii) previous MRI exams of a plurality of patients, iii) medication or medication changes indicated in the first patient specific record, or iv) analysis of IMD data or other data associated with the first patient record that indicates therapy needs, wherein the therapy needs include a) whether A-V conduction condition exists in the first patient, b) sufficient base rate to achieve overdrive pacing, or c) increased pacing output to capture. Optionally, the one or more processors are further configured to determine Smart MRI settings for programming the first IMD associated with the first patient during an MRI exam, the Smart MRI settings determined using i) data analytics, ii) artificial intelligence (AI), or iii) machine learning, and store the Smart MRI settings in the first patient specific record. Optionally, the first patient specific record further comprises an associated second IMD or a summary of a second implanted system.

In accordance with embodiments herein, a healthcare system comprises an MR platform comprising non-transitory memory configured to store program instructions and patient specific records associated with individual patients. Each of the patient specific records includes a summary of an implanted system including an IMD and patient identifying information. The MR platform further comprises one or more processors that, when executing the program instructions, are configured to i) receive MRI settings associated with a first patient specific record, the MRI settings configured to be programmed into a first IMD in advance of an MRI exam, wherein the first IMD is associated with the first patient specific record; ii) store the MRI settings in the first patient specific record; and iii) in response to an input received through a graphical user interface, remotely program the MRI settings into the first IMD in advance of the MRI exam.

Optionally, the one or more processors are further configured to remotely program operational settings into the first IMD after the MRI exam. Optionally, responsive to the one or more processors receiving a confirmation of the MRI settings, the one or more processors are configured to remotely program the MRI settings into the first IMD.

Optionally, the MRI settings are configured to maintain sensing during the MRI exam, wherein the one or more processors are further configured to automatically direct the IMD, when the MRI exam is complete, to i) clear data affected by MRI interference, ii) filter out MRI induced noise and retain clean data, or iii) flag data that is deleted, filtered, or modified based on MRI induced noise.

In accordance with embodiments herein, a healthcare system comprises an MR platform comprising an MRI implant portal configured to provide secure access to information associated with the MR platform. The MR platform also includes non-transitory memory configured to store program instructions and patient specific records associated with individual patients. Each of the patient specific records includes a summary of an implanted system including an IMD and patient identifying information. The MR platform further includes one or more processors that, when executing the program instructions, are configured to i) create a first patient specific record associated with the first patient; ii) store the first patient specific record in the memory; and iii) transmit a code configured to electronically direct a user to the MRI implant portal, wherein the code is associated with the first patient or the first patient specific record.

Optionally, the code is a QR code or a hyperlink. Optionally, the one or more processors, responsive to the MRI implant portal receiving an indication that the code has been activated, are configured to provide access to the patient specific record associated with the first patient.

Optionally, the memory is further configured to store data or hyperlinks associated with i) MR conditions of use associated with a plurality of IMDs, ii) adverse reports associated with a plurality of IMDs, iii) a centralized ledger associated with the first patient or a plurality of patients, the centralized ledger including information associated with a) previous MRI exams, b) previous programmed device parameters, or c) patient outcomes. Optionally, the one or more processors are further configured to determine Smart MRI settings for programming the IMD associated with the first patient during the MRI exam, wherein the Smart MRI settings are based on the information associated with the centralized ledger. Optionally, the one or more processors are further configured to create a digital passport associated with a first patient, the first patient having an associated IMD.

DETAILED DESCRIPTION

Figure 1:
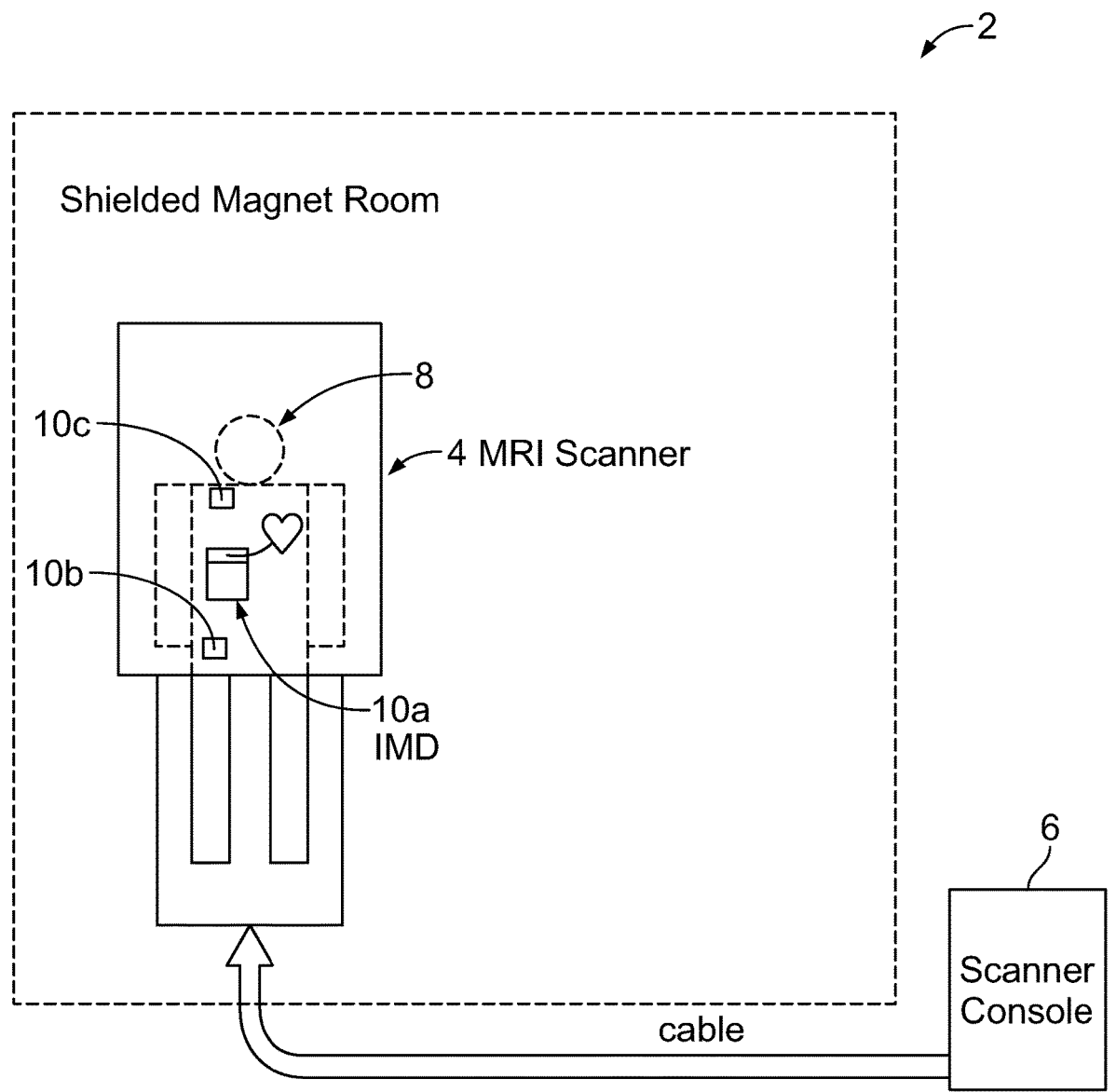
FIG. 1 illustrates an overall magnetic resonance imaging (MRI) system having an MRI scanner operative to generate MRI fields during an MRI procedure (e.g., exam) for examining a patient with one or more IMD.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "MR conditional" shall mean a device and/or system that includes one or more MR conditional implanted device as defined in ASTM F2503 with demonstrated safety in the MRI scanner environment within the defined conditions of use including conditions for the static magnetic field, the time-varying gradient magnetic fields and the radiofrequency fields. Additional conditions, including specific configuration of the device, may be required. It should be understood that other governing documents and/or regulations can define MR conditional implanted devices and thus are equally applicable. The MR conditional device requires coordination and interaction between medical caregivers and the patient prior to and/or after the MRI exam, such as programming of particular settings that control the operation of the MR conditional device during the MRI exam and/or manipulation or deletion of data acquired during the MRI exam.

The term "MR platform", "centralized platform", and "MRI centralized platform" are used interchangeable herein and shall mean a platform including memory(s), processor(s), server(s), database(s), etc. The MR platform can be located in a single location, distributed across two or more physical locations, and/or extended to the cloud (e.g., accessed over the Internet, such as by accessing servers that can be physically distributed). The MR platform stores information that can be used to plan and acquire an MRI exam of a patient with an implantable device. The MR platform can be accessed by a plurality of users and can determine smart MRI settings that can be programmed into an implantable device prior to the MRI exam.

The term "digital passport", "digital MRI passport", and "passport" are used interchangeably herein and shall mean a code, such as a QR code or a hyperlink, or an application that can be utilized, such as by a patient, to electronically direct a user to a centralized MRI implant portal or other electronic location. At the MRI implant portal or other electronic location, the user can access information stored on the MR platform, transmit information to the MR platform to be stored on the MR platform, respond to alerts sent by the MR platform, and communicate with other users of the MR platform. The digital passport can be independent of the MR platform, providing the data previously included on a patient's physical card as described herein. The digital passport also can integrate with an MR platform to provide the access to the centralized MRI implant portal.

The term "MRI settings" shall include settings that are programmed into an implantable device prior to an MRI exam. The MRI settings may be generic and thus not tailored to specific patient needs. The MRI settings may constitute an MRI mode. The term "MRI mode" shall mean a specialized mode of operation associated with an IMD. When the IMD is in MRI mode or the MRI mode is enabled, the IMD can be safely used with MRI. IMDs that do not have a defined MRI mode can still have MRI settings.

The term "Smart MRI settings" shall include settings that are programmed into an implantable device prior to an MRI exam that are tailored to specific patient needs, based on previous MRI scanning history of the patient, and/or based on scanning parameters and history of a plurality of patients. The Smart MRI settings can be determined using data analytics, artificial intelligence (AI), and/or machine learning, and can provide physiologically optimal therapy settings for the patient. Smart MRI settings can be based on analysis of dual chamber pacemaker device heart rate diagnostics, pacing diagnostics, medication and recent medication changes, and whether or not A-V conduction is sensed. The Smart MRI settings can include asynchronous pacing (e.g., pacing mode of DOO), increased base rate to ensure overdrive pacing (e.g., 90 bpm, etc.), and increased pacing output (e.g., 7V at 1 ms, etc.).

The term "MRI implant portal" shall mean a digital entry point or address that provides access to the MR platform, and in some cases, specific patient information, IMD information, manufacturer specific information, etc.

The term "biological signal" shall include electrical signals measured by one or more electrodes or other electrical sensors coupled to an IMD within the patient, where the signals are indicative of a cardiac activity characteristic, hemodynamic characteristic and/or body generated analyte. The electrical signals may be susceptible to MRI induced interference. Nonlimiting examples of biological signals include cardiac activity signals, neurological signals, cardiac impedance, pulmonary impedance, transthoracic impedances, accelerometer signatures, heart sounds, pulmonary arterial pressure signals, blood pressure, MCS rpm levels, MCS flow rates, optical photoplethysmography (PPG) signals, in which a light source emits light to a tissue and the photodetector measures the reflected light from the tissue, and the like.

The terms "body generated analyte" and "BGA" shall mean a test substance or specimen that is naturally generated by or naturally present in a human body. The test substance or specimen may be in liquid form (e.g., blood or other bodily fluid), solid form (e.g., tissue, fat, muscle, bone, or other organ-based material), gas form, cellular form or otherwise. Non-limiting examples of body generated analytes include hematocrit, troponin, brain natriuretic peptide, beta human chorionic gonadotropin (bHCG), carbon dioxide partial pressure (pCO.sub.2), partial pressure oxygen (pO-.sub.2), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody, $TCO_2$, Anion Gap, ionized calcium, urea nitrogen, lactose, hemoglobin, pH, $PCO_2$, $PO_2$, $HCO_3$, Base Excess, $O_2$, ACT Kaolin, ACT Celite, PT/INR, β-hCG, cTnI, CK-MB, BNP and the like, and combinations thereof. The analyte may be tested in a liquid sample that is whole blood, however other samples can be used including blood, serum, plasma, urine, cerebrospinal fluid, saliva and amended forms thereof. Amendments can include diluents and reagents such as anticoagulants and the like. As non-limiting examples, the physiologic BGA characteristic of interest (COI) may relate to diuretic response, CRS, intravascular volume depletion/overload, total body overload, malnutrition, peripheral edema, adenomatous GI tract absorption, liver congestion, liver protein generation state, hypoglycemic, hyperglycemic and the like.

Nonlimiting examples of BGA data include BGA data indicative of a level of an electrolyte COI of a patient. Electrolyte related BGA data may include a glucose level indicative of a blood sugar level for the patient, B-type natriuretic peptide (BNP) data, cardiac enzyme related BGA data (e.g., in connection with determining troponin I or troponin T levels). The method and system may further comprise identifying episodes of increased pulmonary arterial pressure (PAP) associated with a decrease in the blood glucose level, and based thereon, may generate the HF diagnosis that avoids an increase in a dosage of the diuretic prescription.

The terms "cardiac activity signal", "cardiac activity signals", "CA signal" and "CA signals" (collectively "CA signals") are used interchangeably throughout to refer to an analog or digital electrical signal recorded by two or more electrodes positioned transvenously, subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous or transvenous electrodes.

The term "IMD data" shall refer to any and all types of information and signals conveyed from an implantable medical device to a local or remote external device. Non-limiting examples of IMD data include cardiac activity signals (e.g., intracardiac electrogram or IEGM signals), neural activity signals, impedance signals (e.g., cardiac, pulmonary or transthoracic impedances), accelerometer signatures (e.g., activity signals, posture/orientation signals, heart sounds), pulmonary arterial pressure signals, blood pressure, mechanical circulatory support (MCS) rpm levels, MCS flow rates and the like.

The terms "physiologic condition" and "non-physiologic condition" are used to distinguish between a normal/healthy state of a patient condition of interest and an abnormal/unhealthy state of the patient condition of interest, respectively. Non-limiting examples of patient conditions of interest include electrical or hemodynamic cardiac behavior (e.g., normal sinus rhythms, arrhythmias, unstable hemodynamic performance), neurological behavior (e.g., pain, tremors, Parkinson's disease, tinnitus, Alzheimer's disease, and other neurological disorders measurable and treatable within the spine, brain and peripheral muscles), blood pressure, pulse oximetry levels, diabetes and other conditions due to imbalances/deficiencies of body generated analytes.

The term "alert" shall mean a communication and/or device command to be conveyed to one or more individuals (e.g., users, patients, entities, etc.) and/or one or more other electronic devices, including but not limited to, network servers, workstations, laptop computers, tablet devices, smart phones, IMDs and the like. When an alert is provided as a communication, the alert may represent an audio, video, vibratory or other user perceivable medium. The communication may be presented in various formats, such as to display patient information, messages, user directions and the like. The communication is presented on one or more of the various types of electronic devices described herein and may be directed to a patient, a physician, various medical personnel, various patient record management personnel and the like. The communication may represent an identification of a patient diagnosis and various treatment recommendations, MRI settings, request for input from the individual, etc. When an alert is provided as a device command, the alert may represent an electronic command directing a computing device (e.g., IMD, MRI equipment, local external device, server) to perform an action. For example, the action may include but is not limited to directing the following: IMD to provide additional IMD data; IMD to collect additional data and/or another type of data; IMD to deliver a therapy and/or modify a prior therapy (e.g., MRI settings, a pacing therapy, neural stimulation therapy, appetite suppression therapy, drug delivery rate); and a server to analyze further information in the patient medical record and/or from another medical record.

The term "obtain" or "obtaining", as used in connection with data, signals, information and the like, includes at least one of i) accessing memory of an external device or remote server where the data, signals, information, etc., are stored, ii) receiving the data, signals, information, etc., over a wireless communications link between the IMD and a local external device, and/or iii) receiving the data, signals, information, etc., at a remote server over a network connection. The local external device may represent an MRI scanner console, an MRI field monitoring device, and/or RF transceiver coupled to various other computing systems. The obtaining operation, when from the perspective of an IMD, may include sensing new signals in real time, and/or accessing memory to read stored data, signals, information, etc., from memory within the IMD. The obtaining operation, when from the perspective of a local external device, includes receiving the data, signals, information, etc., at a transceiver of the local external device where the data, signals, information, etc., are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc., from local memory and/or from other memory, such as within a cloud storage environment and/or from the memory of a workstation or clinician external programmer.

Embodiments may be implemented in connection with elements of examples of MRI compatible systems that could be used with the new MRI workflow. For example, the MRI centralized platform and/or remote workflow can include one or more structural and/or functional aspects of the device(s), system(s), and/or method(s) described in US Patent Application 20220338809A1, titled "Methods and devices related to operation of an implantable medical device during magnetic resonance imaging" having a publication date of Oct. 27, 2022; US Patent Application 20220339452A1, titled "System for detecting magnetic resonance generated gradient field using an implanted medical device" having a publication date of Oct. 27, 2022; US Patent Application 20190224475 titled "Implantable lead with flexible paddle electrode array" having a publication date of Jul. 25, 2019; US Patent Application 20210187284 titled "Implantable lead with flexible paddle electrode array" having a publication date of Jun. 24, 2021; U.S. Pat. No. 8,600,520 titled "Implantable lead assembly having a plurality of inductors" having an issue date of Dec. 3, 2013; US Patent Application 20180140856 titled "Systems and methods for implantable automatic mri mode enabling" having a publication date of May 24, 2018; U.S. Pat. No. 8,521,304 titled "MRI compatible implantable lead with a distributed band stop filter" having an issue date of Aug. 27, 2013; U.S. Pat. No. 9,293,818 titled "Intra-pericardial medical device" having an issue date of Mar. 22, 2016; U.S. Pat. No. 9,211,406 titled "MRI compatible implantable lead" having an issue date of Dec. 15, 2015; U.S. Pat. No. 8,554,338 titled "MRI-compatible implantable lead having a heat spreader and method of using same" having an issue date of Oct. 8, 2013; U.S. Pat. No. 8,538,553 titled "MRI compatible implantable lead" having an issue date of Sep. 19, 2013; and US Patent Application 20110144722 titled "Mri-compatible implantable lead with improved Ic resonant component" having a publication date of Jun. 16, 2011. The patents, applications and publications listed herein are expressly incorporated by reference in their entireties.

System Overview

In accordance with new and unique aspects herein, systems and methods are described that support workflow for MR conditional implants. The system provides a platform that centralizes access to the many types of information needed by medical professionals and patients. The system provides a portal through which the platform can be electronically accessed by the various users, who are remote from the platform. The platform stores information and/or links to information related to a plurality of medical devices that is required to determine the safety precautions and specific device settings needed for the particular patient's implanted device during the MRI exam. The platform further provides support for and facilitates the scheduling of the MRI exam between multiple users who are remote from each other and the platform.

The platform also stores patient specific information related to the patient and their associated implanted device(s). The platform stores a summary of the patient's implanted system, implant history, specific MR conditions of use appropriate for the implanted devices, IMD settings (e.g., settings to use during an MR exam, normal operational settings, Smart MRI settings), as well as the patient's MRI history. In contrast, conventional systems rely on paper copies conveyed by the patient, time-intensive research between healthcare professionals, and/or manual searching of various websites and paper manuals in an attempt to confirm necessary information. In some cases, the information is not available, or the located information is out-of-date, negatively impacting patient care and outcome as an MRI exam may be delayed or canceled. This can result in increased costs for the patient, health care providers, MRI clinic, etc., as well as worse patient outcomes. Further, patient care is often provided on an emergency basis and during times when a patient's typical care givers may not be available. In an emergency, healthcare personnel need access to accurate information quickly so that the patient can be treated in an expedient manner without causing harm to the patient. Also, patients may be unable to communicate, and thus healthcare personnel need a reliable source of information that is available at any time of day, such as the platform disclosed herein, that integrates all of the necessary information for treating patients who have IMD(s) during MRI exams, and which is available via a plurality of multiple devices that are located remote from the platform. Accordingly, the platform provides a significant improvement to and practical application of the technical field of MR imaging of patients with implanted device(s), improving the safety of both the patient and the implanted device, while also improving the workflow of the medical professionals.

In some cases, remote programming of the implanted device is appropriate for a patient, and the platform facilitates the programming of the patient's implanted device(s) by receiving input, such as via a graphical user interface, from a device and user who are located remotely with respect to the patient and the platform. Remote programming can be used to program the MRI settings into the implanted device prior to the MRI exam, and to program the operational settings into the implanted device once the MRI exam is complete.

The platform can electronically facilitate the identification and saving of MRI settings for the implanted device in advance of the MRI exam, and also facilitate the pre and post MRI exam checks. Additionally, the platform includes MRI data trends, analytics, machine learning, artificial intelligence, etc., whereby the platform analyzes previous MRI scan data associated with the patient and/or a wider population of patients to optimize the MRI settings for the patient (e.g., Smart MRI settings). The Smart MRI settings can be electronically programmed into the IMD via a device associated with the platform (e.g., local to the patient, remote from the patient) to improve the comfort and/or safety of the patient during the MRI exam, improving the patient experience and adherence to prescribed examinations.

Overview of MRI-Responsive Systems

FIG. 1 illustrates an overall magnetic resonance imaging (MRI) system 2 having an MRI scanner 4 operative to generate MRI fields during an MRI procedure (e.g., exam) for examining a patient with one or more IMD. The MRI scanner 4 operates under the control of an MRI scanner console 6, which controls the strength and orientation of the fields generated by the MRI scanner 4 and derives images of portions of a patient 8 therefrom, in accordance with otherwise conventional techniques. MRI systems 2 and imaging techniques are well known and will not be described in detail herein. See, for example, U.S. Pat. No. 5,063,348 to Kuhara et al., entitled "Magnetic Resonance Imaging System" and U.S. Pat. No. 4,746,864 to Satoh, entitled "Magnetic Resonance Imaging System", the complete subject matter of which are incorporated herein by reference. One or more implantable medical device (IMD) 10 is implanted within the patient to receive transmissions of biological signals (e.g., electrophysiological signals and/or hemodynamic signals) sensed within the patient by the IMD 10 during the MRI procedure. The IMD 10 may be constructed in various manners. For example, the IMD 10a may include a lead system for sensing electrophysiological signals within the heart of the patient, and for delivering any needed pacing pulses or shock therapy. In some embodiments, patients 8 can have additional IMDs, such as IMD 10b, 10c that can have different functionality than the IMD 10a.

The IMDs 10 and/or lead system may also include various biological sensors (not separately shown within FIG. 1) for sensing hemodynamic signals or other signals within the patient, such as sensors operative to sense intracardiac pressure, blood oxygen saturation (i.e., blood SO$_2$), blood temperature, body temperature and PPG signals, pulmonary arterial pressure (PAP), etc. In some cases, the sensors may be implanted elsewhere in the patient or may be mounted in or on the IMD 10 itself. In some embodiments, during the MRI procedure, one or more of the IMDs 10 can also analyze the various sensed signals to detect abnormal conditions such as sudden drops in blood pressure, sudden changes in blood temperature, etc. Still further, the lead system can be equipped with one or more temperature sensors (not shown in FIG. 1) for detecting temperatures (e.g., within the IMD 10, within the lead or patient tissue, etc.).

While embodiments herein may illustrate and/or describe electrodes and/or conductors within leads, many of the sensors may also be housed inside the can of the IMD 10. Gradient signals can penetrate inside of the can and therefore be detected by sensor circuitry inside of the housing. Accordingly, implantable cardiac monitors (ICMs) and leadless IMDs, even though they don't have leads, are susceptible to RF and gradient MRI induced noise, to which embodiments herein are applicable.

MRI imaging is complex and will not be described in detail herein. In general, the MRI scanner 4 generates three electromagnetic fields that are used to produce an MRI image. These include a static magnetic field, a time varying gradient magnetic field and a time varying RF field. The time varying gradient magnetic field, more specifically the rapid switching of gradient magnetic fields (gradient ramping) can interfere with sensing of biological signals (e.g., neurological signals, impedance signals, electrophysiological signals) in an IMD 10 as it can invoke non-physiological noise in the IMD's 10 sensing circuitry.

Over the last decide, improvements in MRI safety associated with active implants have resulted in improved MRI accessibility for patients with active IMDs. Active implants can include IMDs such as, but not limited to, pacemakers, cardioverters, neurostimulators, etc. However, the complexities and checks required at each step of an MRI scan referral, such as scheduling, preparation of the patient and the IMD, checks required prior to the MRI exam, the MRI exam itself, and post MRI exam follow-up pose resource and logistical challenges for all users (e.g., patients, implant manufacturer staff, MRI clinic staff, implant clinic/physician offices, etc.). Further, as the population ages, increased availability and indications for MRI exams have scaled up significantly and are expected to further increase.

MRI Implant Portal and Interactions Therewith

Figure 2A:
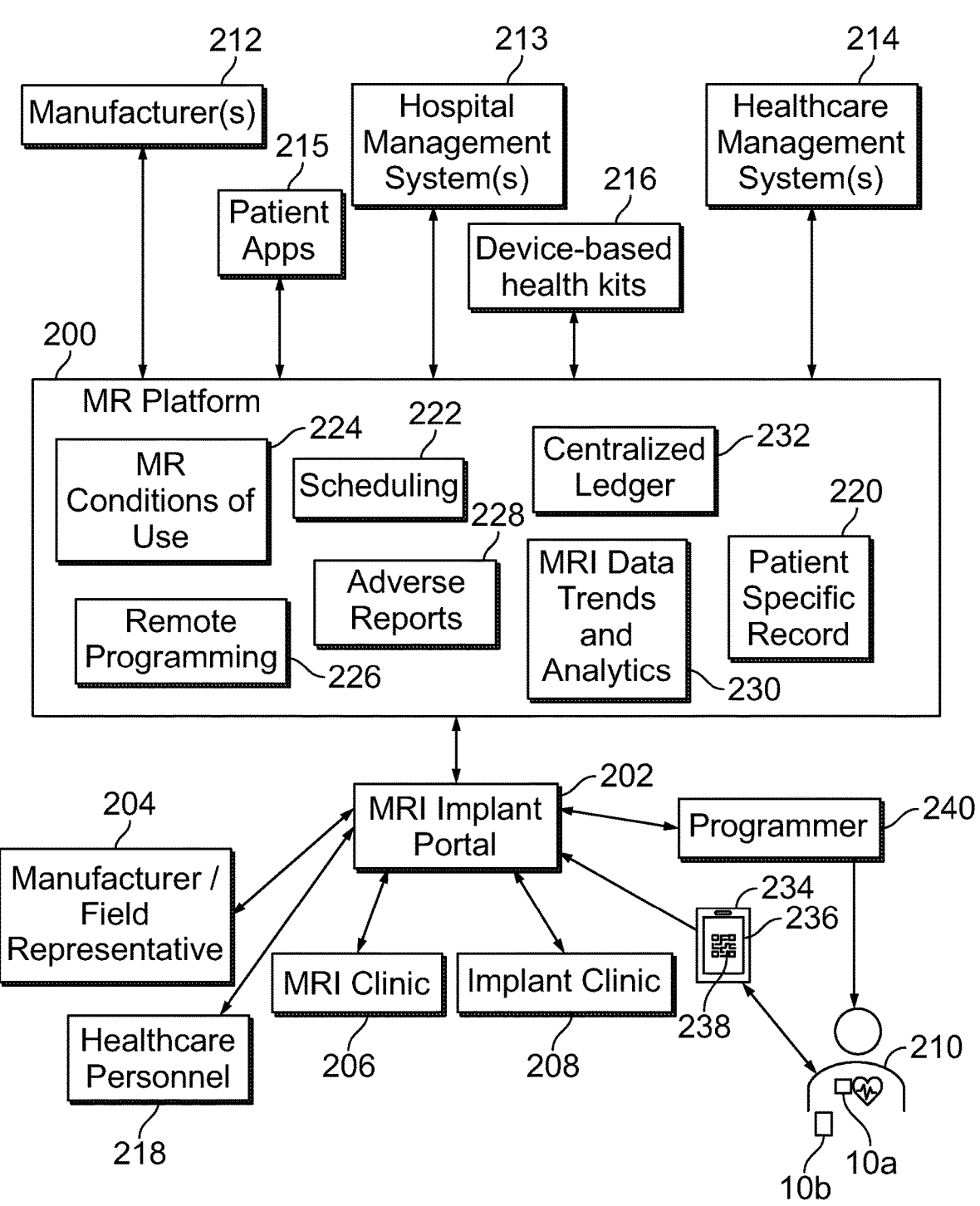
FIG. 2A illustrates an MR platform and MRI implant portal for MR conditional implants and interactions therewith in accordance with embodiments herein.
Figure 2B:
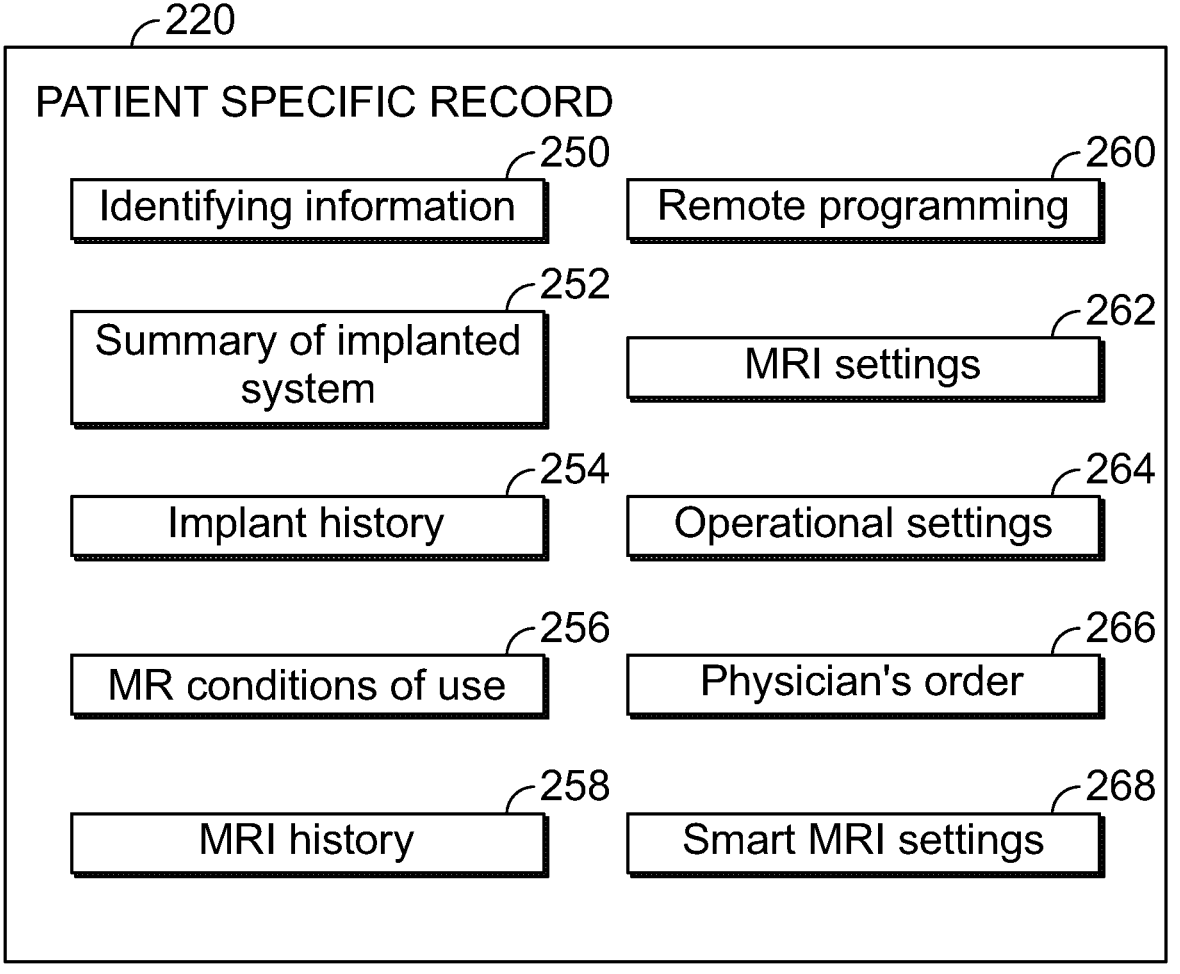
FIG. 2B illustrates an example of data that can be associated with and/or stored in a patient specific record that is stored and/or accessed by the MR platform in accordance with embodiments herein.

FIG. 2A illustrates an MR platform 200 and MRI implant portal 202 for MR conditional implants and interactions therewith in accordance with embodiments herein. FIG. 2B illustrates an example of data that can be associated with and/or stored in a patient specific record 220 that is stored and/or accessed by the MR platform 200 in accordance with embodiments herein. The MR platform 200 and MRI implant portal 202, along with one or more elements further described in FIGS. 2A and 2B can comprise a healthcare system. FIGS. 2A and 2B will be discussed together below.

As discussed herein, the MR platform 200, MRI implant portal 202, and associated MRI workflows for various participants (e.g., users and patients) in the MRI scanning process of patients who have IMDs 10, and especially active IMDs 10, as described herein provide a technical solution to the complications of providing quality healthcare to patients, and further improve efficiencies and patient access to safe MRI exams. The MR platform 200 provides a centralized location that is accessible via the MRI implant portal 202. The MR platform 200 includes and/or provides access to the information needed to i) prepare for an MRI exam, ii) safely accomplish an MRI exam, and iii) ensure the safety of the patient and correct operation of the IMDs 10 throughout the process.

In conventional systems and workflows, only the cardiac physician has access to the patient information. The MR platform 200 provides a practical application for centralizing and consolidating information needed by all users to ensure safe scanning of MRI patients. The MR platform 200 further analyzes patient data, both of the instant patient and across populations, to determine and present Smart MRI settings that provide physiologically optimal therapy settings for the patient, and also improve the patient's and/or healthcare professional's experiences during the MRI exam. The Smart MRI settings can suggest lower settings that have been effective in other patients, and can also suggest settings that are less extreme and thus more comfortable based on data associated with the patient.

Turning first to FIG. 2A, MRI implant portal 202 provides an entry or gateway to the MR platform 200 that supports remote workflow for MR conditional implants and other implantable medical devices. The MRI implant portal 202 conveys information and/or establishes communication between the MR platform 200 and i) manufacturer/field representatives 204, ii) MRI clinics 206 (e.g., in hospital, stand-alone, fixed, mobile, etc.), iii) implant clinics 208, iv) patients 210, and/or v) other healthcare personnel 218. For example, the MRI implant portal 202 receives and conveys messages and alerts, such as through text message, email, applications, ticketing systems, automated telephonic systems, and the like.

The MR platform 200 can communicate with (e.g., request and/or receive information from, push information to, etc.) various other platforms and applications, including implant manufacturer platforms 212, hospital management systems 213, third-party and/or healthcare management systems 214, patient applications 215, and device-based health kits 216 (e.g., smartphone/smartwatch based applications that acquire data from the patient, such as, but not limited to, Apple health, Google Fit, etc.). In some embodiments, the MR platform 200 can provide/transmit a token, code, hyperlink, etc., through the MRI implant portal 202 that can direct a user to a particular location within the implant manufacturer platforms 212, hospital management systems 213, third-party and/or healthcare management systems 214, patient applications 215, and device-based health kits 216.

By way of example, the MR platform 200 can be included within and/or communicate with a manufacturer's new or existing platform (e.g., manufacturer platform 212) such as, but not limited to, Merlin.net™ Patient Care Network of Abbott, located at Abbott Park, IL. The MR platform 200 can also communicate with third party data aggregators and/or utilize third party data aggregator-like services. The MR platform 200 can communicate with multiple manufacturers to provide and request hyperlinks, information, data, etc., associated with implantable devices produced/provided by various manufacturers and/or third parties. In accordance with new and unique aspects, information and data needed for MRI scanning is accessible via the MRI implant portal 202 for every IMD 10 associated with the patient 210.

The MR platform 200 and MRI implant portal 202 can be integrated together or separate from each other. Further, the MR platform 200 can be centralized and/or distributed across multiple servers, locations, etc.

The MRI implant portal 202 can be an entry point to the information stored on the MR platform 200, as well as provide a user interface for accepting and displaying information. The MRI implant portal 202 can provide application-based and/or web-based access to patient specific information that provides each user (e.g., field representatives 204, MRI clinics 206, implant clinics 208, patients 210, and healthcare personnel 218) the optimal level of information and access control as needed to perform their roles. Accordingly, the MR platform 200 can provide controlled access to each user based on their identity and/or function.

Turning to FIG. 2B, patient specific records 220 provide information associated with each patient 210 registered on the MR platform 200. The patient specific records 220 may be organized and maintained within any manner of non-transitory data sources, such as data bases, text files, data structures, libraries, relational files, flat files and the like. In some embodiments the patient specific records 220 can be stored in one or more database or in multiple formats.

The patient specific information that is displayed via the MRI implant portal 202 can depend upon who is accessing the information (e.g., controlled access). For example, the patient 210 may see identifying information including their name, address, and specific implant(s), while other users may not see all of the patient identifying information, but have access to specific programming and product details associated with each of the IMDs 10, patient MRI exam history, etc.

The patient specific record 220 can include, but is not limited to, identifying information 250, such as name and address of the patient 210, date of birth, insurance information, etc. The identifying information can also include medical information, medication and/or medication changes, and history of the patient 210.

A summary of the patient's implanted system 252 stores data such as, but not limited to, the model and/or serial numbers of the IMD 10, other manufacturer identification information, when the IMD 10 was implanted, implant location information (e.g., where the IMD 10 is located within the body of the patient 210), what leads are implanted, what leads are active, lead length, abandoned hardware, such as capped leads, non-functional elements such as non-functional implantable pulse generator, etc. There may be more than one summary of the implanted system 252 if the patient has more than one IMD 10a, 10b.

The patient's implant history 254 can detail historical data of when each of the IMD(s) 10 were implanted, if and when an IMD 10 was removed, reactions to previous and/or current IMDs 10, etc.

MR conditions of use 256 can include and/or link to data associated with the IMD(s) 10. MR conditions of use 256 can detail what steps need to be taken with the patient, the IMD(s) 10, and the MRI scanner 4 to perform a safe MRI exam.

MRI history 258 includes data related to the patient's previous experience with MRI exams, such as a record of when, where, and details (e.g., scan region associated with one or more MRI exam, MRI parameters, etc.) of the MRI exam, what MRI settings were used, any physiological changes after the MRI exam as a result of interaction between the IMD 10 and MRI (e.g., PCT rise trends, etc.) and/or any negative interactions, responses, etc.

Remote programming 260 indicates whether or not remote programming is allowed (i.e., approved) and for which IMDs 10, if multiple IMDs 10 are implanted. For example, approval of remote programming allows a user who is located remotely with respect to the patient 210 to program the IMD 10 via the MRI implant portal 202.

MRI settings 262 can be saved in or associated with the patient specific record 220. In some cases, for example if the patient 210 does not require constant pacing, the MRI settings 262 can indicate that pacing and sensing are turned off. The MRI settings 262 can be based on a physician's order 266, which can be uploaded/input by the implant clinic 208, healthcare personnel 218, etc. In some embodiments, the MRI settings 262 are based on the MR conditions of use 256 and may not be tailored to the patient 210.

Operational settings 264 are stored and can be accessed and programmed into the IMD 10 after the MRI exam via remote programming, local programming, and/or via the MRI implant portal 202. The operational settings 264 can also be referred to as the permanent settings, as the operational settings 264 are programmed into and operate the IMD 10 during normal, or non-MRI mode, operation.

Smart MRI settings 268 can provide more tailored MRI settings for the patient's IMD 10 that can decrease the time needed by the physician to determine the best or most appropriate MRI settings for that particular patient 210. Smart MRI settings can also, in part, be based on the physician's order 266, and are discussed further below. The MRI settings 262, operational settings 264, and Smart MRI settings 268 can be accessed via the MRI implant portal 202, facilitating remote programming, wherein the user is located remotely with respect to the patient 210, and local programming, wherein the user is located proximate the patient 210, such as within the MRI clinic 206.

Returning to FIG. 2A, a scheduling module 222 of the MR platform 200 assists with scheduling the MRI exams. When the MR platform 200 receives an MRI exam referral, such as via the MRI implant portal 202, the scheduling module 222 transmits alerts, such as via the MRI implant portal 202, to one or more users when their input and/or review is needed, required, and/or suggested. The alert can be different or the same for each user, and can be customizable by the receiving user. For example, a patient 210 may wish to receive alerts through a text message, phone call, email, a message or alert on a patient App (discussed further below), etc. The personnel who remotely program a patient's IMD 10 or have other functionality, such as the implant clinic 208, physician offices or other healthcare personnel 218, field representatives 204, and MRI clinic 206 can receive their alert as an entry or record in a queue of an overall workflow, an entry in a ticketing system, etc. For example, the scheduling module 222 or other element of the MR platform 200 can automatically create or generate a case ticket associated with the patient that can be saved, searched, tracked, placed in a queue, etc. The generation of the case ticket can automatically result in the transmission of one or more case ticket alerts to one or more users. Responses to alerts can be received via the MRI implant portal 202, and can result in the display of information, population of data fields, generation of additional alerts, etc.

MR conditions of use 224 are complicated and can change over time based on new versions, field reports, reported failures, known adverse conditions to MRI and/or patients, trends over time, etc. The MR conditions of use 224 can include, but are not limited to, patient and implant specific information, such as dedicated device settings (e.g., MRI settings) for a particular IMD 10, absence of any adverse conditions to MRI, and MRI scanner parameters.

The MR conditions of use 224 can, for example, provide access to documentation of current MR conditions of use for each of the IMDs 10 indicated in the patient specific record 220. For example, documents, links thereto, etc., associated with the MR conditions of use 224 can be saved on the MR platform 200, providing the technical advantage of a consolidated location to compile, collaborate, and review implant specific information needed by the field representative 204, the implant clinic 208, the MRI clinic 206, and the patient 210 that is accessible via the internet and/or an application.

For example, an MR conditions of use document may be viewed and/or downloaded through the MRI implant portal 202. In other embodiments, a link to a current MR conditions of use document, database, etc., may be provided to direct the user to the appropriate manufacturer platform 212 (or other entity). In some embodiments, the MR platform 200 can trigger an alert that is transmitted to the manufacturer platform 212 of a particular IMD 10 to solicit an updated version or confirmation that the current version is the most recent version (i.e., every 6 months, every 12 months, etc.). Although not shown as a separate element, in addition, users can access help/support documents on MRI scanning as needed (e.g., how to lower RF power during MRI scans, image artifact information, etc.).

A remote programming module 226 provides an interface and mechanism to perform, or assist in the performance of, a plurality of tasks remotely, thus moving a significant portion of the MRI workflow to the cloud. For example, one or more of the following tasks can be accomplished remotely, such as from a different location via the MRI implant portal 202, or via the MRI implant portal 202 while in proximity to the patient 210. Tasks can include, but are not limited to: i) confirming that the patient has an MR conditional system, ii) confirming no adverse conditions to MRI are present (e.g., other non-safe implants, documented health conditions, previous adverse reaction to particular settings during a previous MRI exam, lead impedance(s) out of normal range, etc.), iii) generating a report of the patient's permanently programmed parameters (e.g., operational settings 264) that can be saved and linked to within the patient specific record 220, iv) selecting and/or saving MRI settings 262, v) reviewing an MRI checklist to ensure completion (e.g., some tasks may be completed by other users and can be indicated as such interactively), vi) performing a pre-MRI check per physician's order 266, vii) programming the IMD 10 into MRI settings 262 or Smart MRI settings 268 in advance of the MRI exam, viii) programming operational settings 264 into the IMD 10 after the MRI exam (e.g., disabling MRI settings 262), and/or ix) performing post-MRI check per physician's order 266. By remotely accomplishing many or all of the tasks associated with the programming of the IMD 10 and the evaluation of the patient 210, in-person device interrogation by the user (e.g., personnel from the implant clinic 208, MRI clinic 206, and/or field representative 204) is eliminated and/or greatly reduced. This provides a technical advantage as more patients can be scanned within a given amount of time as users can be located remotely, able to service different geographic areas and multiple patients within a short period of time. A further technical advantage is realized as all of the necessary information for the MRI exam and for working with the patient 210 during the scan is consolidated into one location, the MR platform 200, and thus is easily and quickly available to all users who require the information.

Adverse reports 228 are stored and/or hyperlinked to provide access to information that may be adverse to the operation and/or safety of one or more IMD 10. For example, field report information can be filed by any of the users shown in FIG. 2A or can be sourced from a manufacturer platform 212, hospital management system 213, healthcare management system 214, the Food and Drug Administration, and the like. In some cases, one or more adverse report within the adverse reports 228 can be linked to the patient specific records 220 if the patient 210 has the associated IMD 10. Providing the adverse reports 228 in the centralized MR platform 200 improves risk management and patient outcomes in the field of medical imaging as the data is available in near real-time, providing access to data that healthcare professionals are not aware of.

In conventional systems, options for the patient 210 with an IMD 10, such as a pacemaker, are typically either i) pacing off or ii) high output, asynchronous pacing, as defined by the MR conditions of use 224. In contrast, MRI data trends and analytics module 230 tracks patient data over time to provide the patient and physician centric device parameters (e.g., MRI settings 262) for MRI exams based on a centralized ledger 232 and/or other patient and population level data. The MRI data trends and analytics module 230 performs large-scale data analytics and AI on the patient population data. For example, one or more processors of the MR platform 200 can employ statistical tool(s) (e.g., Monte Carlo analysis techniques, neural networks, etc.) and AI algorithm(s), and then utilize the statistical tool(s) and AI algorithm(s) to suggest Smart MRI settings 268. In some embodiments, machine learning/AI algorithms can run on machine learning frameworks (e.g., such as in-house to the manufacturer), and/or standard machine learning frameworks such as TensorFlow, PyTorch, scikit-learn, Spark ML, Keras running on the backend of the portal. Patient population data can be stored in the centralized ledger 232, including previous MRI exams and associated programmed device parameters, at patient (e.g., the patient 210) and population level (e.g., a plurality of patients), and/or accessed via other consolidation locations accessible via the internet.

In some embodiments, the Smart MRI settings 268 can be determined by a data driven AI algorithm that considers information stored in the patient specific record 220, such as the patient's permanently programmed device parameters (e.g., operational settings 264), patient health trends (e.g., included in the patient identifying information 250), MRI history 258 which may include a ledger of previous MRI exams and previous MRI settings of the patient 210, risk factors, the physician's order 266, and/or patient therapy needs. The MRI data trends and analytics module 230 can recommend the patient specific Smart MRI settings 268 to the physician or other user during remote programming, such as with the remote programming module 226, and/or store the Smart MRI settings 268 in the patient specific record 220.

For example, the MRI data trends and analytics module 230 can review data associated with Patient A who has had at least one MRI exam. The MRI data trends and analytics module 230 can review the settings used during the MRI exam, how Patient A responded or reacted to the settings before, during and after the MRI exam (e.g., patient outcomes), and then analyze Patient A's data together with the population data of a plurality of patients. The MRI data trends and analytics module 230 can determine whether settings that provide a lower level of therapy will still provide the benefits needed by Patient A. In accordance with new and unique aspects, the MRI data trends and analytics module 230 can provide the technical benefit of optimizing therapy for patients 210.

In some embodiments, a first use case concerns implantable cardiac devices and other IMDs 10. Smart MRI settings 268 can be based on analysis of device pacing diagnostic trends and diagnosis of the patient 210 as being non-pacer dependent. The MR platform 200 can automatically present and/or store Smart MRI settings 268 in the patient specific record 220 that include Pacing Off.

In other embodiments, a second use case concerns pacemakers and other IMDs 10. Smart MRI settings 268 can be based on analysis of dual chamber pacemaker device heart rate diagnostics, pacing diagnostics, medication and/or recent medication changes, and whether or not A-V conduction is sensed. The Smart MRI settings 268 can include asynchronous pacing (e.g., pacing mode of DOO), increased base rate to ensure overdrive pacing (e.g., 90 bpm, etc.), and increased pacing output (e.g., 7V at 1 ms, etc.). The Smart MRI settings 268 can be stored in the patient specific record 220 and advantageously provide settings that are customized for the patient 210 that can provide physiologically optimal therapy settings for the patient.

In further embodiments, a third use case concerns implantable cardiac monitors (ICM) and other IMDs 10 that maintain sensing during the MRI exam. The MRI data trends and analytics module 230 can utilize AI algorithms to determine, based on MRI noise patterns on device sensed data across patient population(s), what sensed data is affected by MRI interference. After the MR exam is complete, the MR platform 200 can automatically direct the IMD 10, such as via the MRI implant portal 202 and/or the patient App 236, to clear data affected by MRI interference and/or filter out MRI induced noise and retain the clean data. Data that is deleted, filtered, or otherwise modified based on MRI induced noise can be flagged appropriately to avoid confusion.

Interaction with MR Platform

As discussed previously, patients 210 are conventionally provided with a physical card to use during the scheduling of MRI exams. The physical card is provided by the implant manufacturer or implant clinic 208 as a reference to be shared with the MRI clinic 206 during the scheduling of MRI exams, and provides a summary of the patient's implanted system. However, if a change is made to the implanted system, such as to a lead or the IMD 10, a new card must be sent/provided to the patient 210, and the patient 210 must now utilize the new card instead of the old card. Patient compliance for carrying the physical card is low, requiring the MRI clinic 206 to reach out to the implant manufacturer/field representative 204 and/or implant clinic 208 prior to each scan to confirm the implanted system, often through the use of fax or calling a call center staffed with representatives, which is time consuming and expensive for all involved users. Additionally, if the patient 210 has more than one IMD 10, such as both a cardiac ICM and a neurostimulator, separate cards are needed for each IMD 10, and may necessitate calls to different representatives 204, implant clinics 208, etc.

To eliminate the need for the physical card, the patient 210 has a "digital passport" that can be realized through an application (e.g., patient App 236) on their patient device 234 (e.g., smartphone, tablet, watch, computer, etc.). The patient App 236 provides access to the patient specific record 220 via the MRI implant portal 202. In some cases, the patient 210 uses a user login and password, and/or other verification (e.g., biometrics, two-part verification, etc.), as is known in the art, to access the patient App 236. In some cases, the MR platform 200 and/or patient App 236 can generate a QR code 238, a hyperlink, or other access information/graphic that is associated only with the patient 210 that can be shared with other users, such as through email, text, physical proximity, printed or digital image, etc. In accordance with new and unique aspects, patient compliance with providing their implant information is greatly improved as many patients 210 carry a patient device 234 on their person most of the time. Furthermore, the digital passport can be configured to be, in some cases, a standalone application that is used to directly provide the implant information without accessing the MRI implant portal 202.

Once logged onto the patient App 236, the patient 210 can view their patient specific record 220. In some embodiments, the patient 210 may have permission to revise and/or confirm some information, such as insurance information, emergency contact, address, etc. Any updates to this information may trigger an alert that is sent to one or more users, such as the implant clinic 208 and/or MRI clinic 206. Updates are saved within the patient specific record 220 on the MR platform 200, such as in the identifying information 250. In some embodiments, not all information will be available for viewing and/or modification by the patient 210, such as specific parameters for their IMD 10 that can only be changed by medical personnel.

The patient 210 may also be approved to review, for example, their implant information, which provides the advantage of keeping the patient specific page 220 current. The patient 210 may have had an additional IMD 10*b* placed (e.g., insulin pump, hip replacement, etc.) that they wish to report. The patient 210 can provide updated information through the patient App 236 that will trigger an alert that is sent to one or more users.

The patient 210 can use the patient App 236 to participate in the scheduling of their MRI examinations. For example, the patient 210 may have an option to choose between two or more MRI clinics 206, and the patient 210 can send an alert with their QR code to the desired clinic 206. The patient 210 can also send messages through the patient App 236. Who the patient 210 can send messages to may be limited based on the timeline of the scheduling/scanning process. For example, the patient 210 may only be able to send messages to their associated implant clinic 208 or physician office until the order for the MRI exam has been sent to a specific MRI clinic 206. At that time, the patient 210 may receive an alert and then be able to send a message to the MRI clinic 206 and/or participate in the scheduling process, such as through an on-line scheduling tool.

The patient App 236 can communicate with the IMD 10, utilizing the wireless communication protocols provided by the patient device 234 and the IMD 10 (e.g., Bluetooth, etc.). The patient App 236 can facilitate the programming of MRI settings 262 in advance of the MRI exam, revert the IMD settings back to the operational settings 264 after the MRI exam, monitor physiological data collected by the IMD 10, direct the IMD 10 to discard physiological data acquired during the MRI exam that may be corrupt, etc. The patient App 236 may accomplish one or more of these tasks based on input from the patient 210, and/or direction received from another user through the MRI implant portal 202.

Access of Other Users and Interaction with MR Platform

In accordance with new and unique aspects, the patient App 236 can be used by other users as a gateway to program the settings of the IMD 10. For example, the implant clinic 208, field representative 204, etc., can access the patient App 236 remotely, through the MRI implant portal 202, to communicate with the IMD 10. In some embodiments, the patient App 236 accepts an input to put the patient App 236 into a selected mode to allow another user or an approved user to remotely program the IMD 10. In other embodiments, authorized users can be defined in the patient App 236 and/or MRI implant portal 202, eliminating the need for a separate input. This can ensure greater protection for the patient 210 by limiting the number of devices/users the IMD 10 is programmed to communicate with. In other embodiments, the patient's MRI settings 262 and operational settings 264 can be conveyed through the MRI implant portal 202 to a conventional programmer 240 if the patient App 236 is not available.

The implant clinic 208 can access the patient specific record 220 and has access to at least some of the information stored therein. In some embodiments, the implant clinic 208 can receive the QR code 238 from the patient 210, the MR platform 200, or another user, such as through the MRI implant portal 202. The receipt of the QR code 238 can trigger an alert that action is needed. In other embodiments, the implant clinic 208 can scan the patient's QR code 238 displayed on the patient's device 234 by the patient App 236, which will allow the clinician to enter the MRI implant portal 202 and access the patient specific record 220.

Further, in some embodiments, other manufacturers and/or field representatives 204 and healthcare personnel 218 can provide updated information on additional implants or changes to the implanted system(s) directly through the MRI implant portal 202. The ability of the MR platform 200 to save patient and device data and ensure the data is linked properly to the patient specific record 220 to support any combination of implants and implanted systems provides a technical advantage to the field of MRI scanning.

The implant clinic 208 can review and update the patient's implant history 254 and MRI history 258. The implant clinic 208 can access the MR conditions of use 224, 256 for the IMD 10. The implant clinic 208 can also schedule and approve MRI exams, be involved in remote programming, such as by defining parameters and settings, and/or communicating through the patient App 236, programmer 240, or other device to put the IMD 10 into MRI mode and to return the settings to the operational settings 264 once the MRI exam is complete. The implant clinic 208 can interface through the MRI implant portal 202 to accomplish a pre-scan check of the IMD 10 as well as a post MRI check. In some embodiments, the remote programming, pre-MRI check and post-MRI check can be based on the physician's order 266.

The MRI clinic 206 can access the patient's implant history 254 on the patient specific record 220, review and update the MRI history 258, schedule and approve MRI exams, as well as review MRI settings 262. The MRI clinic 206 can further review the MR conditions of use 224, 256, and can communication via the MRI implant portal 202 to generate a query, such as a technical query, on the MR conditions of use 224, 256. In some embodiments, when such a query is entered, the MR platform 200 transmits an alert to the remote programming personnel and/or field representative 204 associated with the IMD 10, lead, etc.

The manufacturer of the IMD 10 can include a plurality of representatives 204 who can access different levels of information associated with the patient 210 via the MRI implant portal 202, such as the patient's implant history 254 and MR conditions of use 256. The representative 204 can review and update the patient's implant history 254 and the MR conditions of use 256. The representative 204 can respond to an alert and address various customer technical queries, such as from the implant clinic 208, the MRI clinic 206, and/or the patient 210.

The representative 204 can review information on scheduled or ordered MRI exams. For example, the representative 204 may receive an alert from the implant clinic 208 and/or MRI clinic 206 advising that the patient 210 requires on-site programming. On-site programming may be required for particular IMDs 10, patients with specific conditions, patients who do not use the patient App 236, etc. In accordance with new and unique aspects, appropriate field representative(s) 204 can be involved in the scheduling process to ensure that on-site support is available to fulfill the physician's order 266 for pre and post MRI programming and verification when the MRI exam is scheduled. In other cases, remote programming is appropriate and the representative 204 can review the proposed schedule to ensure that remote representative(s) 204 are available to accomplish the pre and post MRI programming and verification per the physician's order 266. The representative 204 can also send an alert, through the MRI implant portal 202 and the patient App 236, to the patient 210, such as to arrange the remote and/or in-person pre and post MRI check to ensure that the MRI settings 262 are appropriate for the patient 210 during the MRI exam.

One or more of the representative 204, MRI clinic 206, implant clinic 208, and healthcare personnel 218 can evaluate/review proposed Smart MRI settings 268, such as based on the patient's implant history 254, MRI history 258, and physiological needs on the physician's order 266. Also, one or more of the representative 204, MRI clinic 206, implant clinic 208, and healthcare personnel 218 can review adverse reports 228 associated with the patient's IMD 10 or other implant, and access the patient's implant history 254 and MRI history 258 to analyze whether the adverse report 228 applies in the context of the particular patient 210.

In the systems and processes herein, the MR platform 200 generates and transmits alerts to request input from one or more users, the patient 210, and/or an entity such as a manufacturer or management system, and to inform the one or more users and/or the patient 210 of various statuses within the processes. Alerts can also be sent to provide information. The MR platform 200 also receives alerts as well as the responses thereto, and in some cases the alerts can be stored in the MRI history 258 or other location within the patient specific record 220.

Create Patient Specific Record and Evaluate Remote Programming

Figure 3:
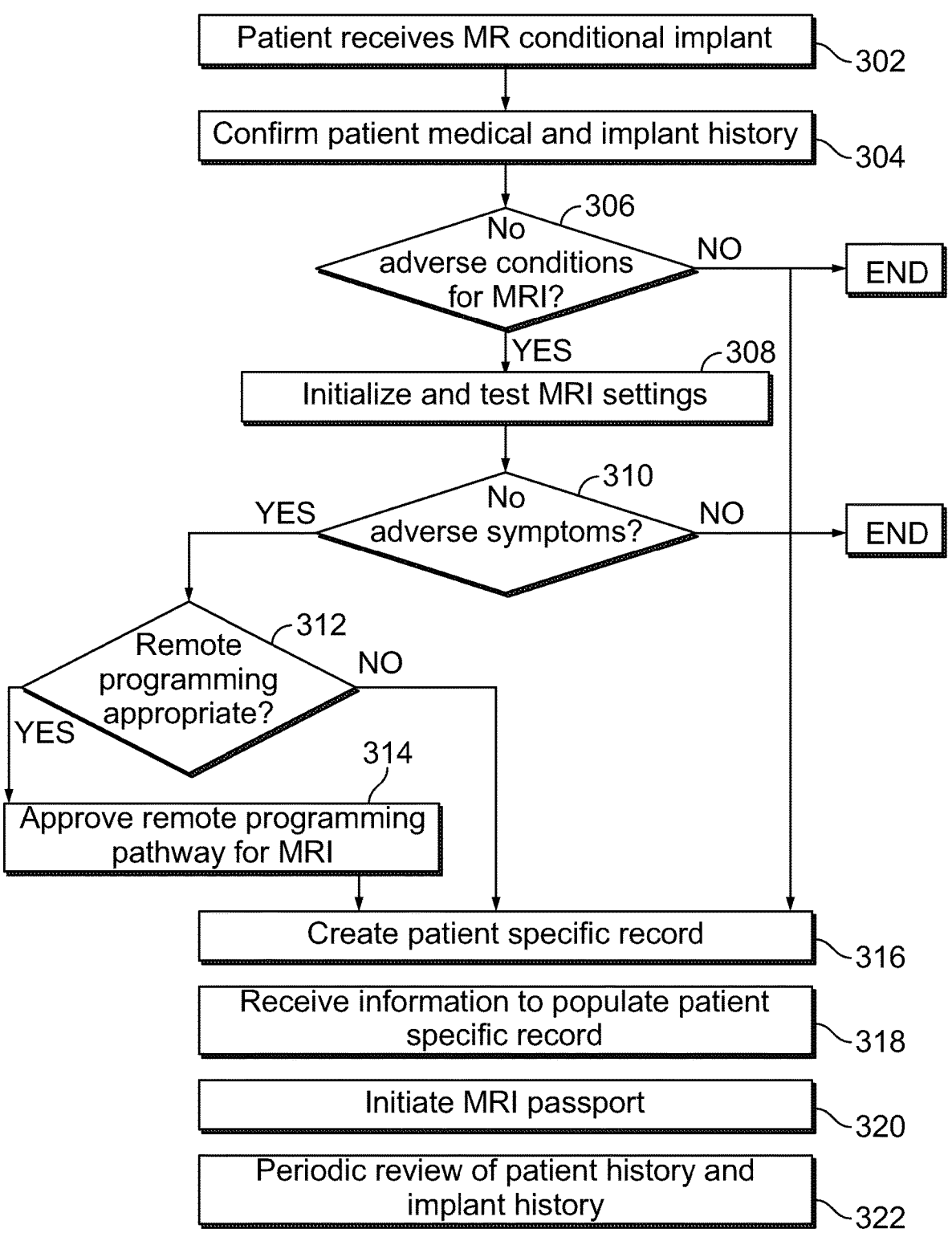
FIG. 3 shows an MR conditional implant process workflow directed to confirming that remote programming is safe for the patient and the IMD, and to initiating the creation of the patient specific record, in accordance with embodiments herein.

FIG. 3 shows an MR conditional implant process workflow directed to confirming that remote programming is safe for the patient 210 and the IMD 10, and to initiating the creation of the patient specific record 220, in accordance with embodiments herein. In some embodiments, this process may electronically take place when the patient 210 in-person such as in the implant clinic 208, a physician's office, or the MRI clinic 206, etc. The operations of FIG. 3 may be implemented by hardware, firmware, circuitry and/or one or more processors housed partially and/or entirely within a local external device, remote server or more generally within a healthcare system. For example, the external devices/systems (e.g., local, remote or anywhere within the health care system) can include memory and one or more processors. In some embodiments, inputs (e.g., keyboard entry, voice entry, gesture entry) to the workflow may be received via a GUI displayed by one or more device, and outputs by the workflow may be displayed on the GUI.

At 302, the patient 210 receives an MR conditional implant (e.g., IMD 10), such as a pacemaker, cardioverter, etc. As discussed previously, the MR conditional implant can have specific requirements that need to be satisfied for the safety of the patient 210 and the IMD 10.

At 304, the user (e.g., physician and/or other medical personnel) can review and confirm the patient's medical history, implant history, and the summary of the implant system that includes details with respect to the IMD 10, leads, etc. The patient's physiological status and risk profile, as well as the IMD 10 need to be at desired levels to ensure that the patient 210 and/or IMD 10 will not be harmed by the MRI exam.

At 306, the user can determine whether the patient 210, IMD 10, and/or other elements of the implant system indicate any adverse conditions that would prevent and/or prohibit the patient 210 from having an MRI exam. For example, a pacemaker cannot rely on the sensed physiological signals of the patient 210 during the MRI exam due to interference, and therefore the sensing capability of the pacemaker is disabled by the MRI settings 262 and the pacemaker is driven at a predetermined pace. In some embodiments, if the patient's physiological signals must be sensed, adverse conditions exist and the method ends or flows to create a patient specific record at 316.

If adverse conditions do not exist at 306, the process flows to 308 and the user can initialize the IMD 10 implanted within the patient 210, and test the MRI settings. The MRI settings can be based on the patient 210 as well as the particular IMD 10 and the implanted system. For example, the MRI settings can take the lead configuration into account. In some embodiments, the MRI settings can be the default settings defined in the MR conditions of use 224. The MRI settings can be sent to the patient's IMD 10 using the programmer 240. In some cases, the MRI settings may turn off at least some of the functionality of the IMD 10.

At 310, the user determines whether the patient 210 has experienced adverse symptoms as a result of the MRI settings that would prevent or prohibit the patient 210 from participating in an MRI exam. In some embodiments, the adverse symptoms can be determined based on patient feedback, ECG data, etc. If adverse symptoms are determined, the process can end or flow to create a patient specific record at 316.

If adverse symptoms are not identified at 310, the process can optionally flow to 312 where the user determines whether remote programming is appropriate for the patient 210. For example, some IMDs 10 may require in-person programming and/or some patients 210 may have conditions that require in-person monitoring. In some cases, remote programming can be approved when the patient 210 does not have access to or the ability to use the patient App 236 and/or requires in-person monitoring. For example, the patient specific record 220 can still be created and may indicate in the remote programming 260 that the programmer 240 or other device is required to convey the signals between the MRI implant portal 202 and the IMD 10. In other embodiments, the physician may approve or not approve remote programming.

If remote programming is feasible and practical for the patient 210 and/or approved by the physician, the process flows to 314 and remote programming is approved.

At 316, the one or more processors of the MR platform 200, responsive to receiving a request for the patient 210 to be added to the MR platform 200, automatically create the patient specific record 220. The request can be received through the user interface of the MRI implant portal 202, which can be accessed via the internet.

In some embodiments, physicians and/or patients 210 may wish to have access to the MR platform 200 even if MRI scanning is not approved at 308. For example, the patient 210 may have multiple implants wherein one of the IMDs 10 is not approved for MRI scanning. The patient specific record 220 can be created to provide access to the most current information available related to the IMDs 10, and to provide access and messaging between users.

At 318, the one or more processors of the MR platform 200 receive information through the user interface of the MRI implant portal 202 to populate the patient specific record 220. For example, the user may populate a graphical user interface (GUI) displayed by the MRI implant portal 202 with at least a minimum of required information and the one or more processors and one or more memories of the MR platform 200 receive the data. The one or more processors of the MR platform 200 create the patient specific record 220, receive patient history and/or patient identifying information 250, the MRI settings 262, etc., and indicate whether the patient 210 is approved for remote programming 260. In some embodiments, additional data related to the patient 210, such as their tolerance of the MRI settings 262, can also be stored in the patient specific record 220.

At 320, the one or more processors of the MR platform 200 optionally initiate creation of the patient's digital MRI passport. The digital MRI passport can be shared with the patient digitally and/or on a physical card, allowing the patient 210 to access their patient specific record 220 through the MRI implant portal 202. The user and/or the one or more processors of the MR platform 200 can share a QR code 238 with the patient 210 that can be used to access the patient App 236, and/or print a physical card (e.g., receipt, etc.) with the QR code 238 for the patient 210. It should be understood that other sign-on information may be shared, such as temporary password, etc. In some embodiments, an MRI approval alert can be transmitted to the patient 210, such as through the patient App 236 and communicated via a GUI, noise, vibratory alert, other accessible notification, etc., indicating that the patient 210 is now registered and, if applicable, approved for remote programming. In other embodiments, the patient's digital MRI passport can be created separate from the workflow of FIG. 3. For example, the digital MRI passport can be created any time after the patient receives an MR conditional implant, regardless of remote programming availability, approval, etc. In still further embodiments, a different application, platform, device platform, device-based health kits, third-party software, etc., can be used to communicate with the MRI implant portal 202 and thus the MR platform 200.

At 322, after a period of time (e.g., 3 months, 6 months, 1 year, etc.), a periodic review of some or all of the information stored and/or linked to in the patient specific record 220 can be initiated. For example, the one or more processors of the MR platform 200 can transmit a patient reevaluation alert to the physician and/or other user, which may be added to a queue of requests. The patient reevaluation alert can include a code (e.g., QR code, hyperlink, etc.) that links to the patient specific record 220 through the MRI implant portal 202. The alert can prompt the user to update and/or confirm the patient specific record 220 (e.g., patient medical history and/or identifying information 250, implant history 254, MRI history 258, remote programming 260, etc.) through the MRI implant portal 202.

Figure 4:
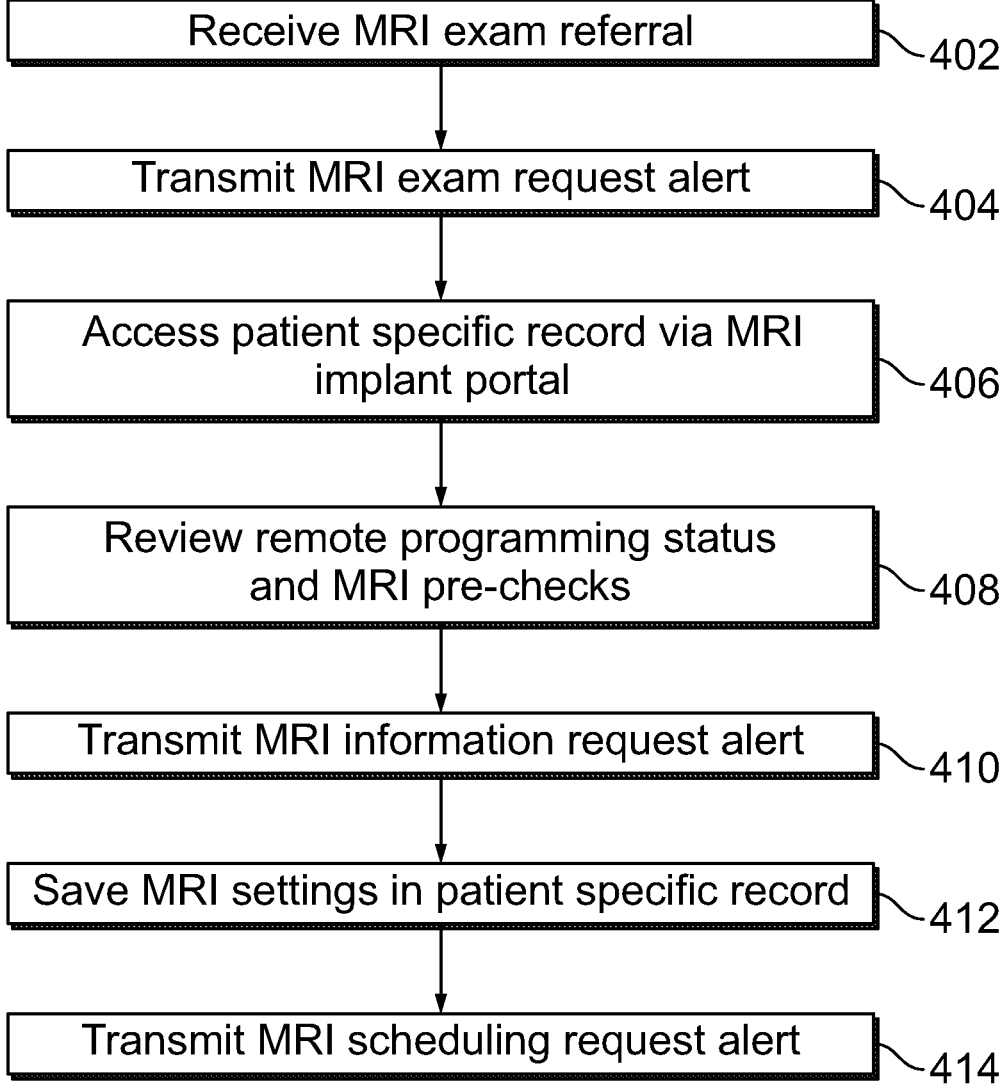
FIG. 4 shows a process workflow for scheduling an MRI exam and saving the MRI settings in the MR platform in accordance with embodiments herein.

FIG. 4 shows a process workflow for scheduling an MRI exam and saving the MRI settings in the MR platform 200 in accordance with embodiments herein. The operations of FIG. 4 may be implemented by hardware, firmware, circuitry and/or one or more processors housed partially and/or entirely within a local external device, remote server or more generally within a healthcare system. For example, the external devices/systems (e.g., local, remote or anywhere within the health care system) can include memory and one or more processors. In some embodiments, inputs (e.g., keyboard entry, voice entry, gesture entry) to the workflow may be received via a GUI displayed by one or more device, and outputs by the workflow may be displayed on the GUI.

At 402, an MRI exam referral is electronically received by the MR platform 200. For example, the user (e.g., physician and/or other medical personnel) can request an MRI exam for the patient 210 through the MRI implant portal 202. The MRI implant portal 202 can be accessed, for example, through a patient's associated QR code 238. Alternatively, the user can log onto the MRI implant portal 202 and search for the patient 210 (e.g., the patient specific record 220) in a GUI, and the MRI exam referral can be associated with the patient specific record 220.

In some embodiments, when the MRI exam referral is received, the MR platform 200 automatically creates/generates a case ticket associated with the patient that can be saved, searched, tracked, placed in a queue, etc. The generation of the case ticket can automatically result in the one or more processors of the MR platform 200 transmitting one or more case ticket alerts to one or more users. The case ticket can thus be updated and/or modified by one or more users, forwarded to other users, used to track the progress of the MRI exam request and scheduling, as well as the accomplishment of the MRI exam.

At 404, the one or more processors of the MR platform 200 automatically transmit one or more MRI exam request alert(s). In some embodiments, an MRI exam request alert is electronically sent to the selected MRI clinic 206 and the implant clinic 208, and may be placed in a queue of other alerts and notifications associated with the patient 210 and/or other patients. In other embodiments, the alert may be an automated phone call, a text message, an email, etc. The queue can be associated with the MR platform 200 and/or can include patients not included on the MR platform 200.

At 406, in response to receiving the MRI exam request alert, the user (e.g., personnel at the MRI clinic 206, etc.) can electronically access the patient specific record 220 through the MRI implant portal 202, such as by using a QR code 238 or other access information that may be provided with the MRI exam request alert. In some embodiments, the MRI clinic 206 can confirm that the clinic is able to perform the requested MRI exam.

At 408, the user can determine whether remote programming is allowed and review critical and non-critical MRI pre-checks. The user can access the MR conditions of use 224, 256 associated with the patient's IMD(s) 10. For example, if the patient 210 has more than one IMD 10, there can be more than one patient specific MR conditions of use 256 that the user can access through the MRI implant portal 202. The user can review the remote programming 260 to verify the patient's remote programming status. The user can also review other information associated with the patient 210 that is stored in the patient specific record 220, such as, but not limited to, the MRI history 258 and implant history 254. In some cases, the access of the user is restricted based on the identity of the user, such as to block access to patient protected information within the identifying information 250, etc.

In some embodiments, at 410, in response to receiving a request from the user at the MRI clinic 206 electronically, such as via a GUI, the one or more processors of the MR platform 200 can automatically transmit one or more MRI information request alerts to other users, such as to raise queries for implant manufacturer's staff (e.g., field representative 204), the patient 210, and/or the implant clinic 208.

At 412, in response to receiving the MRI exam request alert sent at 404, the implant clinic 208 can electronically access the MRI implant portal 202, such as by using a QR code 238 sent via the MRI exam request alert. The implant clinic 208 can clear (e.g., approve) the patient 210 for the MRI exam, and review, input, and/or save the MRI settings 262. In some embodiments, the MRI settings 262 can be input through the MRI implant portal 202, such as via a GUI, and saved to the patient specific record 220. The MRI settings 262 can be based on the physician's order 266. The user can further review, approve, and share patient specific Smart MRI settings 268 to the MRI clinic 206 via the MRI implant portal 202. In some embodiments, some or all of the Smart MRI settings 268 can be used to populate the MRI settings 262. It should be understood that users other than the implant clinic 208 may be responsible for populating the MRI settings 262.

At 414, serially or simultaneously with other steps in the workflow, the scheduling of the MRI exam can be accomplished either by a user at the MR clinic 206 or can be accomplished through on-line scheduling, such as by the one or more processors of the MR platform 200 automatically transmitting one or more MRI scheduling request alerts. The MRI scheduling request alerts can be transmitted to the patient 210, the MR clinic 206, the field representative 204, and/or implant clinic 208, and may depend upon who will be involved in the MRI exam (e.g., who will accomplish the IMD 10 programming in-person or remotely). Each of the participants/groups may be sent a QR code 238 or other hyperlink to access the MRI implant portal 202 to view and/or make one or more selections to the on-line scheduling. The MRI scheduling alerts can be sent via automated telephone, email, text, fax, the patient App 236, sent to a queue of tasks associated with a user or group, etc.

It should be understood that many of the steps during the scheduling of the MRI exam and programming the MRI settings 262 can be accomplished in a different order than discussed. Further, in some embodiments the patient specific record 220 may show a list or other graphical representation of the alerts transmitted and/or resolved that is visible to one or more users and/or the patient 210, allowing the users involved to visualize the progress within the workflow.

Figure 5:
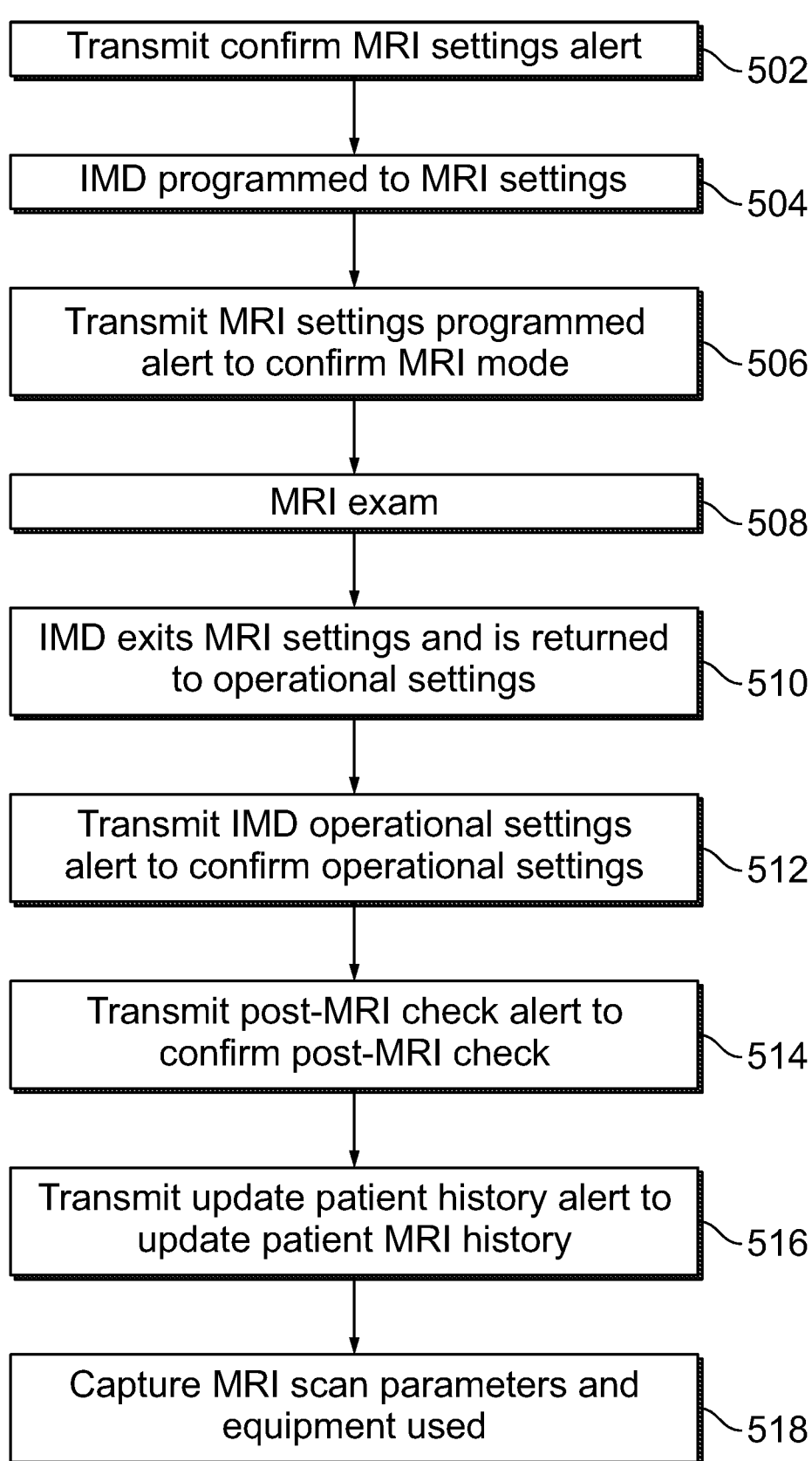
FIG. 5 shows a process workflow for acquiring the patient's MRI exam in accordance with embodiments herein.

FIG. 5 shows a process workflow for acquiring the patient's MRI exam in accordance with embodiments herein. The operations of FIG. 5 may be implemented by hardware, firmware, circuitry and/or one or more processors housed partially and/or entirely within a local external device, remote server or more generally within a healthcare system. For example, the external devices/systems (e.g., local, remote or anywhere within the health care system) can include memory and one or more processors. In some embodiments, inputs (e.g., keyboard entry, voice entry, gesture entry) to the workflow may be received via a GUI displayed by one or more device, and outputs by the workflow may be displayed on the GUI.

At 502, the MR platform 200 generates a confirm MRI settings alert that is transmitted to one or more users associated with the MRI exam (e.g., the MRI clinic 206, implant clinic 208, other healthcare personnel 218, field representative 204). The MR platform 200 can receive, via the MRI implant portal 202, confirmation that the MRI settings 262 associated with the patient's IMD(s) 10 have been completed and confirmed (if necessary). For example, the MRI settings 262 can be accessed and viewed through the patient App 236 (e.g., GUI), the MRI implant portal 202 (e.g., GUI, accessed via the QR code 238, web-based, hyperlink), etc.

At 504, the IMD 10 is programmed to the MRI settings 262. If the patient 210 has more than one IMD 10, this step is accomplished for each IMD 10, if necessary. The programming of the MRI settings 262 can be initiated i) by a remotely based healthcare worker or user, such as through a GUI, ii) based on a timed schedule that automatically programs the IMD 10 to the MRI settings 262 at a predetermined date and time, iii) via the patient App 236, such as through a GUI, that communicates with the MRI implant portal 202, iv) via the programmer 240, such as through a GUI, in the MRI clinic 206 that receives the MRI settings 262 via the MRI implant portal 202, v) from a user manually, vi) via another electronic device and/or application, vii) in response to a request received by the MRI implant portal 202, such as from a user or other electronic device, or viii) by auto-detect, such as when the IMD 10 automatically senses (e.g., with a sensor or other functionality within the implanted system) the fields of an MRI environment. In some cases, the IMD 10, such as an implantable glucose monitor, a loop recorder, cardiac monitor, or a neuromodulator, may be directed by the patient App 236 or other wireless connection to turn some or all of the functionality off, enter a stand-by mode for a period of time, or be pre-programmed to turn off at a specific time, etc. In some embodiments, the patient App 236, programmer 240, and/or MRI implant portal 202 can convey a confirmation to the MR platform 200 in response to the IMD 10 being programmed to the MRI settings 262.

Secure remote programming of the IMD 10, remote programming protocols, validation of external devices to facilitate communication sessions with the IMD 10, and the like, can be accomplished with structure and functionality described in at least U.S. Application Ser. No. 63/380,420, entitled "SYSTEM AND METHOD FOR IMPLANTABLE MEDICAL DEVICE REMOTE PROGRAMMING" filed Oct. 21, 2022; U.S. Application Ser. No. 63/367,064, entitled "SYSTEM AND METHOD FOR IMPLANTABLE MEDICAL DEVICE REMOTE PROGRAMMING" filed Jun. 27, 2022; U.S. application Ser. No. 17/805,823, entitled "SYSTEM AND METHOD FOR IMPLANTABLE MEDICAL DEVICE REMOTE PROGRAMMING" filed Jun. 7, 2022, and U.S. application Ser. No. 18/337,282, entitled "SYSTEM AND METHOD FOR IMPLANTABLE MEDICAL DEVICE REMOTE PROGRAMMING" filed Jun. 19, 2023, which are incorporated by reference herein in their entireties.

At 506, in response to the IMD 10 being programmed to the MRI settings 262 and/or receiving the alert/confirmation of 504, the MR platform 200 automatically transmits an electronic MRI settings programmed alert confirming that the IMD 10 has entered MRI mode prior to scanning. In some embodiments, the MRI settings programmed alert can be sent to a plurality of users involved with the MRI exam such as the MRI clinic. In other embodiments, the MRI settings programmed alert can be initiated in response to receiving information via the MRI implant portal 202.

At 508, the MRI exam is accomplished under MRI conditions of use, and in some embodiments, advanced life support (ALS) or device support staff (e.g., field representative 204, MRI clinic staff, implant clinic staff, etc.) may provide assistance.

At 510, following completion of the MRI exam, the IMD 10 is returned to the operational settings 264. For example, the IMD 10 can be programmed out of or instructed to return to the operational settings 264 in response to i) a notification sent by the patient App 236, ii) a notification sent by the MR platform 200 via the MRI implant portal 202, iii) a notification sent by a programmer 240 on-site, a remote programmer 240, or other external device, or iv) a time-out may expire, automatically triggering the operational settings 264 to be loaded into the IMD 10. In some embodiments, the patient App 236, MRI implant portal 202, programmer 240, or other external device can direct an IMD 10, such as a loop recorder, cardiac monitor, etc., that remained functional during the MRI exam to delete a predetermined amount of stored scan data that may have been corrupted by the MR signals during the MRI exam.

At 512, in response to confirmation that the IMD 10 has returned to the operational settings 264, the MR platform 200 automatically transmits an IMD operational settings alert. The confirmation can be generated by the IMD 10, the patient App 236, a local or remote programmer 240, the MR platform 200, based on signals from the IMD 10, a user, etc.

At 514, the MR platform 200 automatically transmits a post-MRI check alert to ensure that users confirm that the IMD 10 is operating as intended and the patient 210 requires no further care associated with the operational settings 264. The post-MRI check alert can be transmitted via the MRI implant portal 202 to the MRI clinic 206, implant clinic 208, programmer 240, field representatives 204, and/or other involved users. The post-MRI check can be accomplished locally, remotely, or a combination thereof. In some embodiments, remote users can utilize data collected by the patient App 236 and conveyed to the MR platform 200 via the MRI implant portal 202 to view signals, settings, etc., of the IMD 10. In other embodiments, remote personnel/representatives can utilize a wireless connection to visualize signals and settings. For example, if the IMD 10 is a pacemaker, pacing capture thresholds may need to be adjusted after the MRI exam to ensure that the pacing capture thresholds are strong and/or high enough to capture the heart. In some embodiments, the operational settings 264 can be reoptimized during the post-MRI check and/or later during a typical follow-up exam (e.g., 3-6 months later, etc.). In some embodiments, when MR platform 200 automatically transmits the post-MRI check alert, the MR platform 200 also closes the case ticket that was generated above at 402. In some embodiments the case ticket can be closed at a later time/date in response to one or more alerts and/or modifications to the case ticket.

At 516, the MR platform 200 automatically transmits an update patient history alert. The update patient history alert can be transmitted via the MRI implant portal 202 to the MRI clinic 206, implant clinic 208, programmer 240, field representatives 204, the patient 210, and/or other involved users. For example, one or more users can update the MRI history 258 stored in the patient specific record 220 of the MR platform 200. The updates can also be based on data automatically collected, such as via the patient App 236 and/or programmer 240, and/or can be input through the MRI implant portal 202.

At 518, the MR platform 200 captures the MRI scan parameters that were used, scan regions, etc., and the specifics of the MRI equipment (e.g., RF coil, etc.) used for the exam. If needed, one or more additional alert can be automatically transmitted to solicit the information, such as from the MRI clinic 206.

Healthcare System

Figure 6:
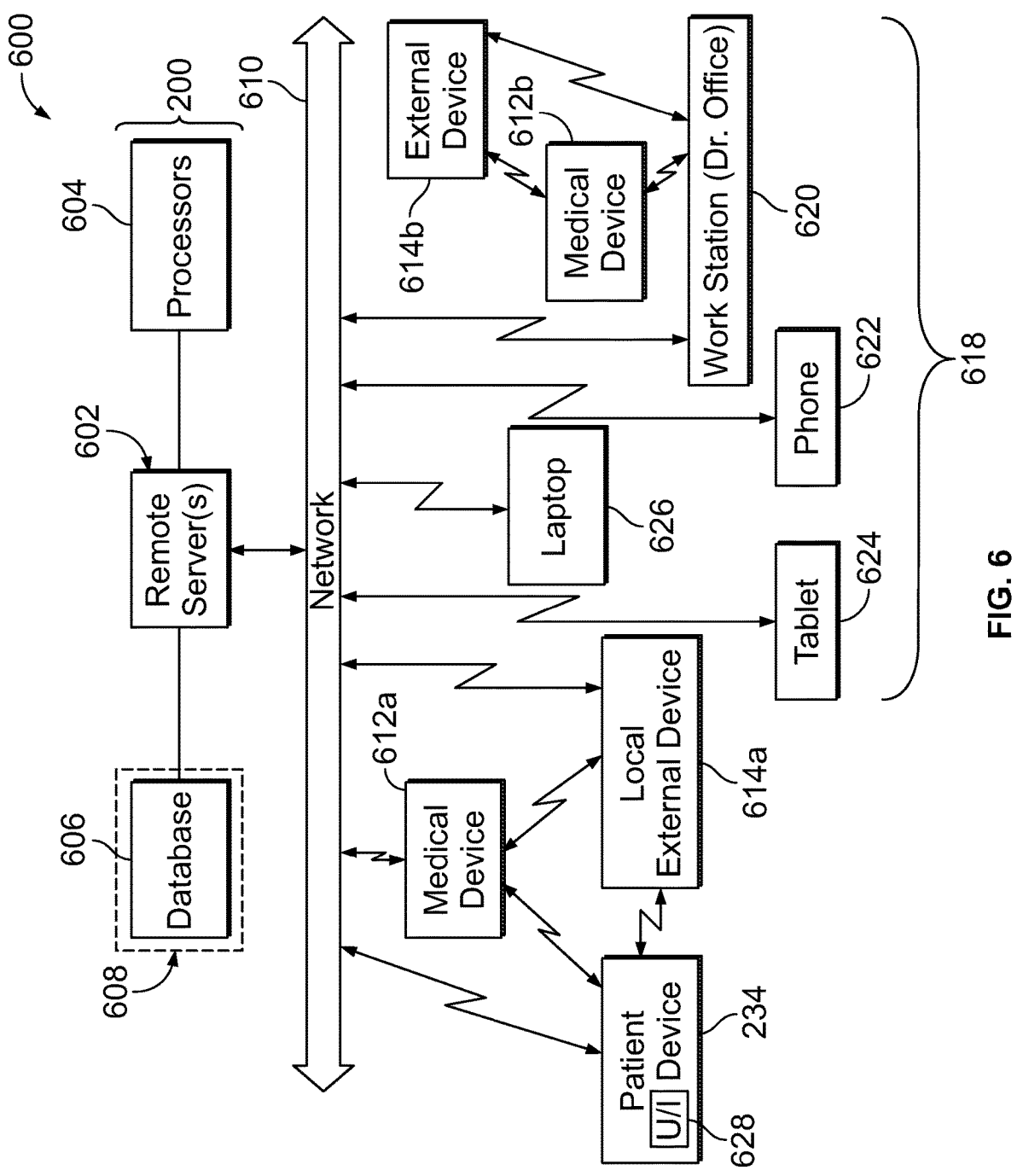
FIG. 6 illustrates a healthcare system including the MR platform interfacing with a plurality of networked devices formed in accordance with embodiments herein.

FIG. 6 illustrates a healthcare system 600 including the MR platform 200 interfacing with a plurality of networked devices formed in accordance with embodiments herein. The MR platform 200 includes one or more servers 602 and one or more processors 604 connected to one or more databases 606 that are stored in one or more non-transitory memory 608. By way of example, the memory 608 can store the patient specific records 220, the scheduling module 222, the MR conditions of use 224, the remote programming module 226, the adverse reports 228, the MRI data trends and analytics module 230, and the centralized ledger 232. The servers 602, database(s) 606, and processors 604 can be located at a common physical location and/or distributed between multiple remote locations within a city, state, country, region, and/or the world.

The server(s) 602 communicate with one or more network 610. The network 610 may be a private network, the internet, a voice over IP (VoIP) gateway, a local plain old telephone service (POTS) such as a public switched telephone network (PSTN), a cellular phone-based network, wireless network, the World Wide Web, a local area network (LAN), a campus area network (CAN), a metropolitan area network (MAN), a wide area network (WAM), RF, a combination of one or more networks, and the like. The servers 602 and the associated devices described herein may wirelessly communicate with one another utilizing various protocols, such as Bluetooth, MICS, GSM, infrared wireless LANs, HIPER-LAN, 3G, satellite, as well as circuit and packet data protocols, and the like. Alternatively, a hard-wired connection may be used to connect the servers 602 and devices. The network 610 facilitates the transfer/receipt of information such as IMD data, data stored on the MR platform 200, data stored in patient specific records 220, and the like.

The system 600 also includes one or more medical devices 612, one or more local external devices 614, one or more patient devices 234 and one or more medical personnel (MP) devices 618, all of which communicate (directly or indirectly) through the network 610 to the servers 602 (e.g., the MR platform 200) and/or one another. The medical device 612 may be passive or active, may collect various types of data, such as cardiac electrical and/or mechanical activity data, PAP or other pressure related data, impedance data, RPM data, flow data, be an IMD 10, and the like.

The patient device 234 includes a user interface 628 through which the patient 210 or other user can view and interact with the MRI implant portal 202. The user can input patient data, IMD data, implant system data, internal and external medical device data, etc. Optionally, the patient device 234 may include one or more microphones that are configured to listen for audible information spoken by a user or patient 210, such as a verbal statement to enter patient data. Optionally, the patient device 234 may include one or more cameras that are configured to capture still images and/or video. The patient device 234 includes also one or more processors, memory, a display, a network communications interface, and various other mechanical components, electrical circuits, hardware and software to support operation thereof. Other devices, such as the tablet 624, phone 622, workstation 620, laptop 626, and external device 614 can include some or all of the same functionality as the patient device 234.

The user interface 628 may include a variety of visual, audio, and/or mechanical devices. For example, the user interface 628 can include a visual input device such as an optical sensor or camera, an audio input device such as a microphone, and a mechanical input device such as a keyboard, keypad, selection hard and/or soft buttons, switch, touchpad, touch screen, icons on a touch screen, touch sensitive areas on a touch sensitive screen and/or any combination thereof. Similarly, the user interface 628 can include a visual output device such as a liquid crystal display screen, one or more light emitting diode indicators, an audible output device such as a speaker, alarm and/or buzzer, and a mechanical output device such as a vibrating mechanism. The display may be touch sensitive to various types of touch and gestures. As further examples, the user interface 628 may include a touch sensitive screen, a non-touch sensitive screen, a text-only display, a smart phone display, an audible output (e.g., a speaker or headphone jack), and/or any combination thereof. The user interface 628 permits the user to select one or more of a switch, button or icon in connection with various operations of the patient device 234.

The local external device 614 may be implemented as a variety of non-implantable devices including, but not limited to, a programmer 240 configured to program MRI settings 262 and operational settings 264 into the medical device 612, and acquire cardiac signals from the surface of a person (e.g., ECGs), and/or intra-cardiac electrogram (e.g., IEGM) signals from the medical device 612. The local external device 614 may reside in a patient's home, a hospital, a physician's office, and/or be interconnected to a patient's skin surface. The local external device 614 communicates wired or wirelessly with one or more medical device 612 and/or the network 610.

In other embodiments, the local external device 614 can be a medical monitoring and/or medical services delivery device, BGA test devices, a local RF transceiver and a user workstation, smart phone, tablet device, laptop computer, desktop computer and the like. The local external device 614 may also be configured to communicate with the MR platform 200 via the network 610, and may display the GUI associated with the MRI implant portal 202, and may allow input from the external device 614 and access to information stored in the patient specific record 220, such as the MRI settings 262 and the operational settings 264. Optionally, the local external device 614 may represent a local RF transceiver that interfaces with the network 610 to upload IMD data and/or BGA data.

Accordingly, the medical devices 612 and external devices 614 deliver a particular treatment for a medical condition such as pacing, shocking, and the like for arrhythmia (e.g., VA, VT, AF, etc.) and/or other heart conditions, treatment of BGA conditions based on measurements of BGA test devices, and the like. Further, the medical devices 612 and/or external devices 614 deliver the particular treatment which transforms, such as in the case of arrhythmia, the patient's heart from an arrhythmia state to a normal sinus rhythm state.

The MP devices 618 may also be implemented as a variety of devices including, but not limited to, programmer 240, workstation 620, smart phone 622, tablet device 624, laptop computer 626, desktop computer and the like. Functionality of the MP devices 618 related to embodiments herein may be implemented through dedicated hardware circuits, firmware, software, and/or applications configured to interface with the MR platform 200 operating on one or more computing devices.

Other servers and memory systems (not shown) can receive data from the devices for storage, retrieval, data collection, data analysis, diagnosis, treatment recommendations and the like. Other databases and file structures (not shown) store all or various portions of the information described herein, including, but not limited to, IMD data, medical record information, treatment diagnoses and recommendations, and the like.

For example, in some embodiments, a healthcare system 600 comprises an MR platform 200 that has non-transitory memory 608 configured to store program instructions and patient specific records 220 associated with individual patients 210. Each of the patient specific records 220 includes information associated with an implantable medical device (IMD) 10 and a patient 210. One or more processors 604 that, when executing the program instructions, are configured to receive a magnetic resonance imaging (MRI) exam referral 402 requesting an MRI exam associated with a first patient specific record 220 from within the patient specific records 220. The first patient specific record 220 has an associated first IMD 10 and a first patient 210. Responsive to the MRI exam referral 402, the one or more processors 604 automatically transmit an MRI exam request alert 404. Responsive to receiving a response to the MRI exam request alert, the one or more processors 604 provide access to the first patient specific record 406. The one or more processors 604 receive MRI settings 262 associated with the first patient specific record 220 that are configured to be programmed into the first IMD 10 in advance of the MRI exam. The one or more processors 604 store the MRI settings in the patient specific record.

In some embodiments, the MR platform 200 is configured to integrate with an existing device platform (e.g., manufacturer platform 212, etc.), a patient application 215, third-party healthcare management systems (e.g., hospital management system 213, healthcare management system 214, etc.) or device-based health kits 216. In other embodiments, wherein responsive to the MRI exam referral 402, the one or more processors 604 generate an exam referral 402 (e.g., ticket) associated with the first patient. In yet further embodiments, the one or more processors 604 are configured to receive a query.

In some embodiments, the memory 608 is further configured to store MRI conditions of use 224 associated with a plurality of IMDs 10 or links to the MRI conditions of use associated with the plurality of IMDs 10. In other embodiments, the memory 608 is further configured to store adverse reports 228 associated with a plurality of IMDs 10 or links to the adverse reports associated with the plurality of IMDs 10. In further embodiments, the memory 608 is further configured to store a centralized ledger 232 including data associated with a plurality of patients 210. In still further embodiments, the memory 608 is further configured to store MRI history 258 associated with the first patient specific record 220, wherein the MRI history 258 includes information associated with one or more previous MRI exams of the first patient 210. In yet other embodiments, the information associated with the one or more previous MRI exams includes i) MR scanner information, ii) MRI scan parameters, or iii) scan regions associated with the one or more previous MRI exams.

In some embodiments, the one or more processors 604 are further configured to, responsive to receiving the MRI exam referral 402, automatically transmit an MRI scheduling request alert 414 to i) IMD programming personnel, ii) field representative 204, iii) the first patient 210, iv) an MRI clinic 206, v) a physician's office, or vi) an implant clinic 208. In other embodiments, the one or more processors 604 are further configured to, in response to receiving a response to the MRI scheduling request alert, provide controlled access to the first patient specific record 220, wherein the level of control is based on a respondent to the MRI scheduling request alert, wherein the controlled access includes displaying information accessible to the respondent.

In further embodiments, the one or more processors 604 are further configured to, responsive to receiving the MRI exam referral 402, automatically transmit an MRI scheduling request alert 414, and responsive to receiving a response to the MRI scheduling request alert 414, display scheduling data associated with the MRI exam request via a portal 202.

In still further embodiments, the one or more processors 604 are further configured to determine Smart MRI settings 268 for programming the first IMD 10 associated with the first patient 210 during an MRI exam, wherein the Smart MRI settings 268 are based on information associated with i) previous MRI exams of the first patient 210, ii) previous MRI exams of a plurality of patients 210, iii) medication or medication changes indicated in the first patient specific record, or iv) analysis of IMD data or other data associated with the first patient record 220 that indicates therapy needs, wherein the therapy needs include a) whether A-V conduction condition exists in the first patient 210, b) sufficient base rate to achieve overdrive pacing, or c) increased pacing output to capture. In some embodiments, the one or more processors 604 can be further configured to store the Smart MRI settings 262 in the first patient specific record 220. In other embodiments, the first patient specific record 220 further comprises an associated second IMD 10 or a summary of a second implanted system 252.

In some embodiments, a healthcare system 600 comprises an MR platform 200 that has non-transitory memory 608 configured to store program instructions and patient specific records 220 associated with individual patients 210. Each of the patient specific records 220 includes a summary of an implanted system 252 including an IMD 10, and patient identifying information 250. One or more processors 604 that, when executing the program instructions, are configured to receive MRI settings 262 associated with a first patient specific record 220. The MRI settings 262 are configured to be programmed into a first IMD 10 in advance of an MRI exam, and the first IMD 10 is associated with the first patient specific record 220. The one or more processors 604 are configured to store the MRI settings in the first patient specific record 220, and remotely program the MRI settings 262 into the first IMD 10 in advance of the MRI exam.

In some embodiments, a healthcare system 600 comprises an MR platform 200 having an MRI implant portal 202 configured to provide secure access to information associated with the MR platform 200. Non-transitory memory 608 is configured to store program instructions and patient specific records 220 associated with individual patients 210. Each of the patient specific records 220 includes a summary of an implanted system 252 including an IMD 10 and patient identifying information 250. One or more processors 604 that, when executing the program instructions, are configured to i) create a first patient specific record 220 associated with the first patient 210, ii) store the first patient specific record 220 in the memory 608, and iii) transmit a code configured to direct a user to the MRI implant portal 202, wherein the code is associated with the first patient 210 or the first patient specific record 220.

Example IMD

Figure 7:
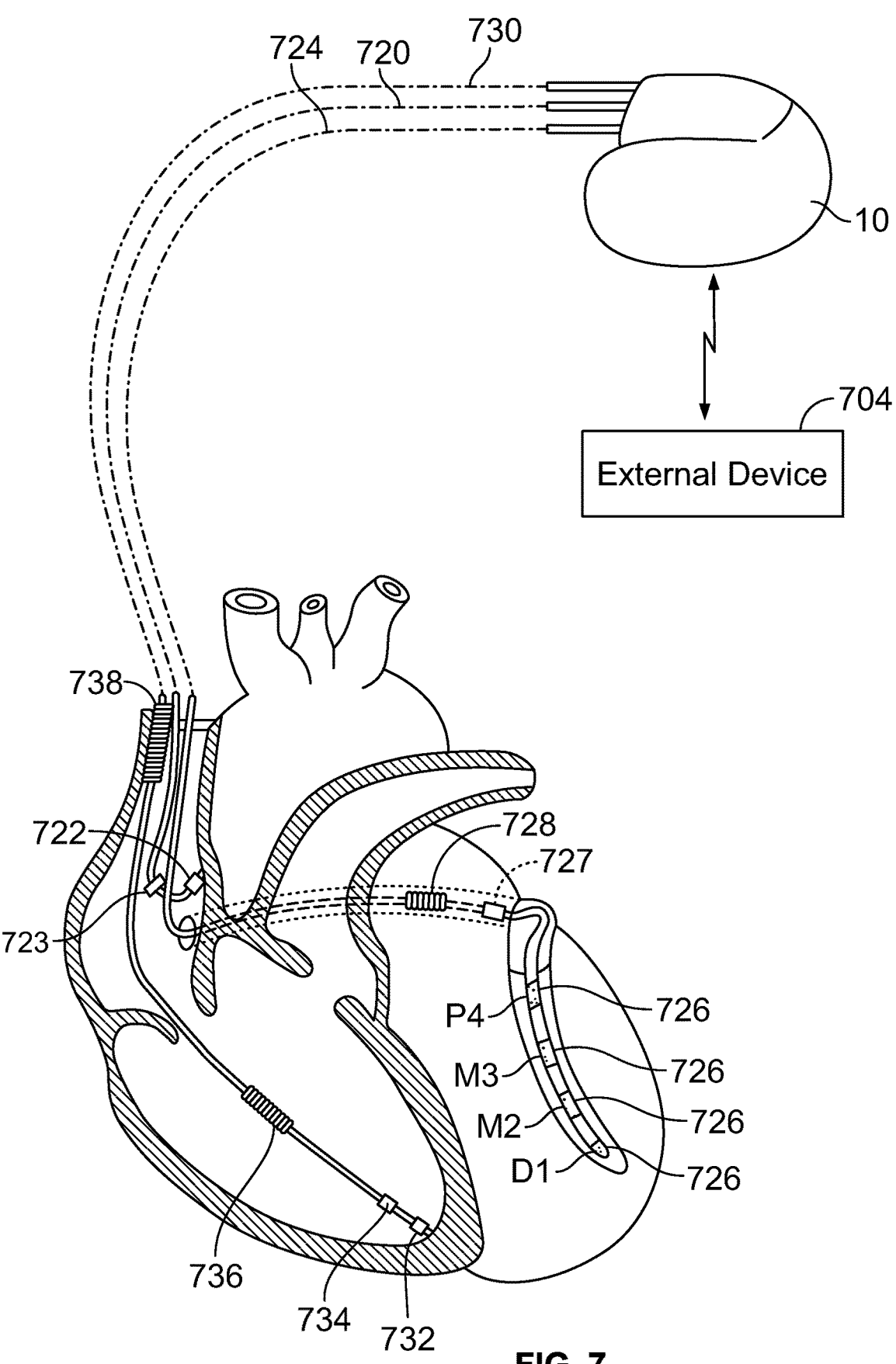
FIG. 7 illustrates an IMD coupled to a heart in a patient and an external device configured to communicate with the IMD implemented in accordance with embodiments herein.

FIG. 7 illustrates an IMD 10 coupled to a heart in a patient 210 and an external device 704 configured to communicate with the IMD implemented in accordance with embodiments herein. The IMD 10 is one example of the type of device that may collect CA signals as biological signals. The external device 704 may be a programmer (e.g., programmer 240 as shown in FIG. 2A), an external defibrillator, a workstation, a portable computer, a personal digital assistant or a cell phone (e.g., the patient device 234 as shown in FIG. 2A), a bedside monitor and the like. The IMD 10 may represent a cardiac monitoring device, pacemaker, cardioverter, cardiac rhythm management device, defibrillator, neurostimulator, leadless monitoring device, leadless pacemaker and the like, implemented in accordance with embodiments herein. The IMD 10 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 10 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like.

The IMD 10 includes a housing that is joined to a header assembly that holds receptacle connectors connected to a right ventricular lead 730, a right atrial lead 720, and a coronary sinus lead 724, respectively. The leads 720, 724 and 730 measure cardiac signals of the heart. The right atrial lead 720 includes an atrial tip electrode 722 and an atrial ring electrode 723. The coronary sinus lead 724 includes a left atrial ring electrode 727, a left atrial coil electrode 728 and one or more left ventricular electrodes 726 (e.g., also referred to as P1, M1, M2 and D1) to form a multi-pole LV electrode combination. The right ventricular lead 730 includes an RV tip electrode 732, an RV ring electrode 734, an RV coil electrode 736, and an SVC coil electrode 738. The leads 720, 724 and 730 detect IEGM signals that are processed and analyzed, and the leads 720, 724 and 730 also delivery therapies.

Information about the IMD 20, the leads 720, 724, 730, and the associated electrodes can be stored within the summary of implanted system 252 of the patient specific record 220. Any changes to the system and/or any elements of the system can be recorded in the implant history 254.

Implantable Medical Device

Figure 8:
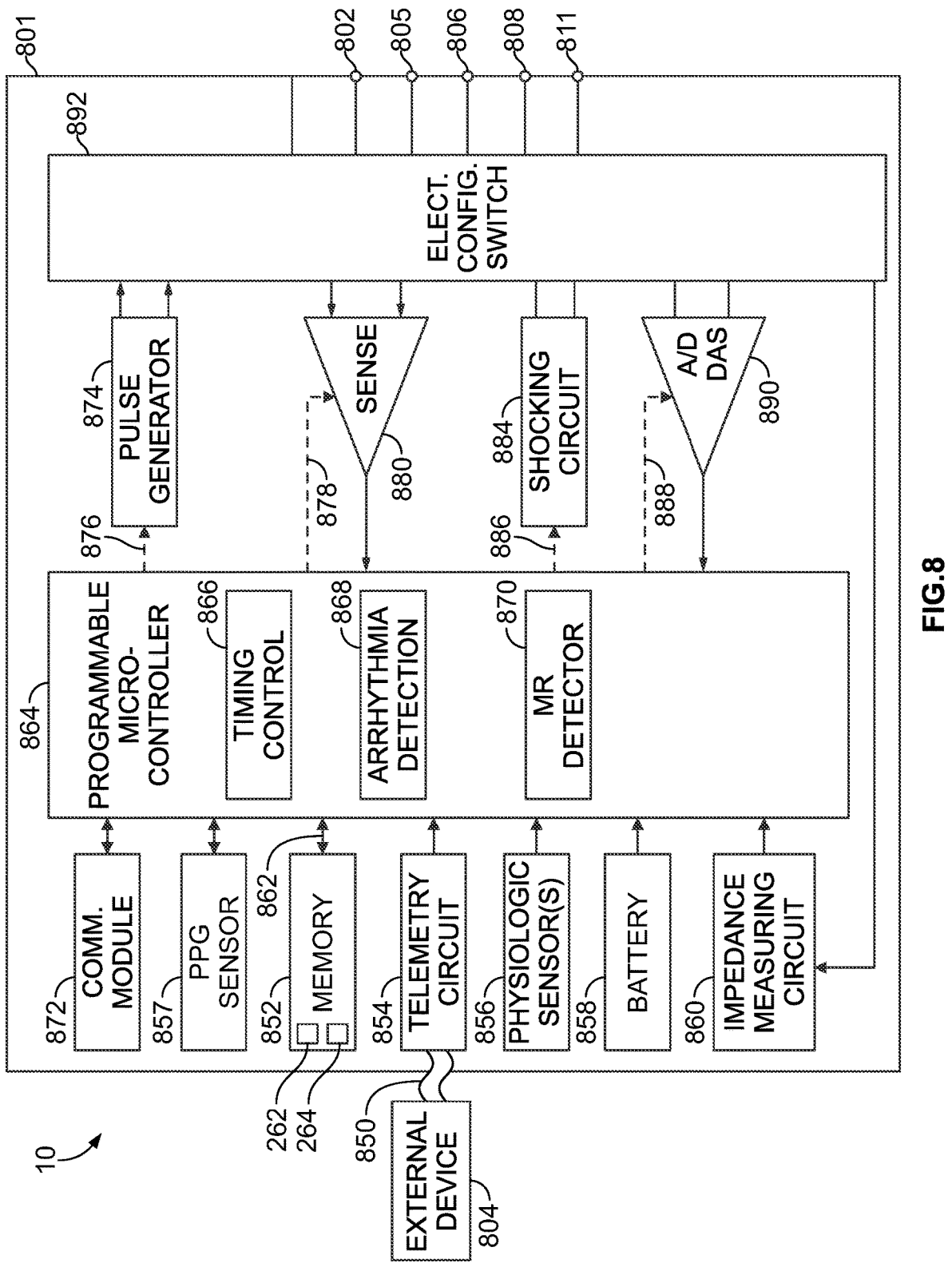
FIG. 8 illustrates a block diagram of the IMD of FIG. 1 in accordance with embodiments herein.

FIG. 8 illustrates a block diagram of the IMD 10 of FIG. 1 in accordance with embodiments herein. The IMD 10 may be implemented as a full-function biventricular pacemaker, equipped with both atrial and ventricular sensing and pacing circuitry for four chamber sensing and stimulation therapy (including both pacing and shock treatment). Optionally, the IMD 10 can provide full-function cardiac resynchronization therapy. Alternatively, the IMD 10 may be implemented with a reduced set of functions and components. For instance, the IMD 10 may be implemented without ventricular sensing and pacing or provide cardiac monitoring only.

The IMD 10 has a device housing 801 to hold the electronic/computing components. The device housing 801 (which is often referred to as the "can", "case", "encasing", or "case electrode") may be programmably selected to act as the return electrode for certain stimulus modes. The device housing 801 further includes a connector (not shown) with a plurality of terminals 802, 805, 806, 808, and 811. The terminals may be connected to electrodes that are located in various locations within and about the heart. The type and location of each electrode may vary. For example, the electrodes may include various combinations of ring, tip, coil and shocking electrodes and the like. One or more electrodes or other electrical sensors are coupled to the sensing circuitry 880 and configured to measure signals indicative of at least one of a cardiac activity characteristic or hemodynamic characteristic or, in accordance with alternative types of IMDs measure a body generated analyte. The biological signals including at least one of cardiac activity signals, cardiac impedance, pulmonary impedance, transthoracic impedances, accelerometer signatures, heart sounds, pulmonary arterial pressure signals, blood pressure, mechanical circulatory support (MCS) rpm levels, or MCS flow rates.

The IMD 10 includes a programmable microcontroller 864 configured to control various operations of the IMD 10, including cardiac monitoring and stimulation therapy. Microcontroller 864 includes one or more microprocessors or CPUs (or equivalent control circuitry), RAM and/or ROM memory, logic and timing circuitry, state machine circuitry, and I/O circuitry. The memory is configured to store program instructions executable by the microcontroller

864 to perform the operations described herein, as well as the overall sensing, analyzing and therapy delivery functionality.

The IMD 10 further includes a pulse generator 874 that generates stimulation pulses for delivery by one or more electrodes coupled thereto. The pulse generator 874 may deliver pacing pulses, anti-tachycardia pacing therapy and the like. The pulse generator 874 is controlled by the microcontroller 864 via control signal 876. The pulse generator 874 is coupled to the select electrode(s) via an electrode configuration switch 892, which includes multiple switches for connecting the desired electrodes to the appropriate I/O circuits, thereby facilitating electrode programmability.

The microcontroller 864 is illustrated to include timing control circuitry 866 to control the timing of the stimulation pulses (e.g., pacing rate, atrio-ventricular (AV) delay, atrial interconduction (A-A) delay, or ventricular interconduction (V-V) delay, etc.). The timing control circuitry 866 may also be used for the timing of refractory periods, blanking intervals, noise detection windows, evoked response windows, alert intervals, marker channel timing, and so on. The timing control circuitry 866 may also be utilized to control the blanking intervals applied to the sensing circuitry 880 during active field intervals of RF and/or gradient fields. Microcontroller 864 also has an arrhythmia detector 868 for detecting arrhythmia conditions, and to review and analyze one or more features of the morphology of cardiac signals. Although not shown, the microcontroller 864 may further include other dedicated circuitry and/or firmware/software components that assist in monitoring various conditions of the patient's heart and managing pacing therapies. The arrhythmia detector 868 can be configured to analyze the biological signals for an indication that the patient is experiencing the non-physiologic condition.

The microcontroller 864 includes an MR detector 870 configured to determine when the IMD 10 is within the MR field. The MR detector 870 can initiate the programming of MRI settings, such as the MRI settings 262 accessed via the patient App 236 through the MRI implant portal 202. The MR detector 870 is also configured to determine when the IMD 10 is outside of the MR field, and can initiate the programming of the operational settings 264.

The operating parameters of the IMD 10 may be non-invasively programmed into the memory 852 through a telemetry circuit 854 in telemetric communication via communication link 850 with the external device 804. For example, the telemetry circuit 854 can use, but is not limited to, high frequency modulation, for example using RF, Bluetooth, or Bluetooth Low Energy telemetry protocols. The telemetry circuit 854 allows intracardiac electrograms and status information relating to the operation of the IMD 10 (as contained in the microcontroller 864 or memory 852) to be sent to the external device 804 through the established communication link 850.

The external device 804 can be any of the devices discussed herein, such as the patient device 234, the programmer 240, any device utilized by the field representative 204, MRI clinic 206, implant clinic 208 and healthcare personnel 218 to access the IMD 10 and/or the MRI implant portal 202.

The memory 852 can also include MRI settings 262 that can be downloaded via the MRI implant portal 202, and operational settings 264. The MRI settings 262 may be stored indefinitely or for a period of time, after which the MRI settings 262 are erased.

The IMD 10 is equipped with a communication module (modulator/demodulator) 872 to enable wireless communication with other devices, implanted devices and/or external devices, such as external device 804. The signals are transmitted in a high frequency range and will travel through the body tissue in fluids without stimulating the heart or being felt by the patient. The communication module 872 may be implemented in hardware as part of the microcontroller 864, or as software/firmware instructions programmed into and executed by the microcontroller 864. Alternatively, the communication module 872 may reside separately from the microcontroller as a standalone component. The communication module 872 facilitates data retrieval from a remote monitoring network. The communication module 872 enables timely and accurate data transfer directly from the patient 210 to an electronic device utilized by a physician.

The IMD 10 includes sensing circuitry 880 selectively coupled to one or more electrodes that is configured to obtain biological signals (e.g., cardiac activity signals, neurological activity signals, and the like) indicative of a physiologic or non-physiologic condition of interest over a period of time. For example, the sensing circuitry 880 performs sensing operations through the switch 892 to detect the presence of cardiac activity in the right chambers of the heart. The sensing circuitry 880 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 880 is connected to the microcontroller 864 which, in turn, triggers or inhibits the pulse generator 874 in response to the absence or presence of cardiac activity. The sensing circuitry 880 receives a control signal 878 from the microcontroller 864 for purposes of controlling the gain, threshold, polarization charge removal circuitry (not shown), and the timing of any blocking circuitry (not shown) coupled to the inputs of the sensing circuitry.

The IMD 10 further includes an analog-to-digital (A/D) data acquisition system (DAS) 890 coupled to one or more electrodes via the switch 892 to sample cardiac signals across any pair of desired electrodes. The data acquisition system 890 is configured to acquire intracardiac electrogram signals, convert the raw analog data into digital data, and store the digital data for later processing and/or telemetric transmission to an external device 804 (e.g., the patient device 234, a programmer 240, local transceiver, or a diagnostic system analyzer). The data acquisition system 890 is controlled by a control signal 888 from the microcontroller 864.

The microcontroller 864 is coupled to the memory 852 by a suitable data/address bus 862. The programmable operating parameters used by the microcontroller 864 are stored in memory 852 and used to customize the operation of the IMD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The IMD 10 may further include one or more physiologic sensors 856. Such sensors are commonly referred to as "rate-responsive" sensors because they are typically used to adjust pacing stimulation rates according to the exercise state of the patient. However, the physiological sensor 856 may further be used to detect changes in cardiac output, changes in the physiological condition of the heart, or diurnal changes in activity (e.g., detecting sleep and wake states). Signals generated by the physiological sensors 856 are passed to the microcontroller 864 for analysis. The microcontroller 864 responds by adjusting the various pacing parameters (such as rate, AV Delay, V-V Delay, etc.) at which the atrial and ventricular pacing pulses are administered. While shown as being included within the unit 10, the physiologic sensor(s) 856 may be external to the unit 10, yet still be implanted within or carried by the patient. Examples of physiologic sensors 856 might include sensors that, for example, sense respiration rate, pH of blood, ventricular gradient, activity, position/posture, minute ventilation (MV), and so forth.

A PPG sensor and PPG sensing circuitry 857 may be provided to collect PPG signals analyzed in accordance with embodiments herein. The microcontroller 864, when executing the program instructions, is configured to analyze the PPG signals for an indication that the patient is experiencing the non-physiologic condition, such as an abnormal, unhealthy state of a patient's condition corresponding to at least one of the following: arrhythmias, unstable hemodynamic performance, pain, tremors, Parkinson's disease, tinnitus, Alzheimer's disease, blood pressure, pulse oximetry levels, or diabetes.

A battery 858 provides operating power to all of the components in the IMD 10. The battery 858 is capable of operating at low current drains for long periods of time, and is capable of providing high-current pulses (for capacitor charging) when the patient requires a shock pulse (e.g., in excess of 2 A, at voltages above 2 V, for periods of 140 seconds or more). The battery 858 also desirably has a predictable discharge characteristic so that elective replacement time can be detected. As one example, the IMD 10 employs lithium/silver vanadium oxide batteries.

Optionally, the IMD 10 further includes an impedance measuring circuit 860, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 860 is coupled to the switch 892 so that any desired electrode may be used. Optionally, the microcontroller 864 further controls a shocking circuit 884 by way of a control signal 886. The shocking circuit 884 generates shocking pulses of low (e.g., up to 0.5 joules), moderate (e.g., 0.5-10 joules), or high energy (e.g., 1311 to 40 joules), as controlled by the microcontroller 864.

The IMD 10 may be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 864 further controls the shocking circuit 884 by way of the control signal 886. The shocking circuit 884 generates shocking pulses of low (e.g., up to 0.5 joules), moderate (e.g., 0.5-10 joules), or high energy (e.g., 11 to 40 joules), as controlled by the microcontroller 864. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD 100.

It is recognized that the configurations of circuitry and microcontrollers illustrated herein are by way of example only. Optionally, operations described in connection with the microcontroller may be implemented by circuitry (e.g., firmware and/or discrete circuitry). Optionally, operations described in connection with the circuitry (e.g., firmware and/or discrete circuitry) may be implemented by the microcontroller 864.

IMDs and Processes for Inclusion with Alternative Embodiments

Embodiments herein may be incorporated with the structure and functionality (e.g., secure remote programming of an IMD, remote programming protocols, communication circuits, remote programming engine, validation of external devices to facilitate communication sessions, etc.) described in any or all of the publications referenced herein, including the following: U.S. Application Ser. No. 63/380,420, entitled "SYSTEM AND METHOD FOR IMPLANTABLE MEDICAL DEVICE REMOTE PROGRAMMING" filed Oct. 21, 2022; U.S. Application Ser. No. 63/367,064, entitled "SYSTEM AND METHOD FOR IMPLANTABLE MEDICAL DEVICE REMOTE PROGRAMMING" filed Jun. 27, 2022; U.S. application Ser. No. 17/805,823, entitled "SYSTEM AND METHOD FOR IMPLANTABLE MEDICAL DEVICE REMOTE PROGRAMMING" filed Jun. 7, 2022; U.S. Patent Publication Number 2021/10370077, entitled "Implantable medical device using permanent and temporary keys for therapeutic settings and related methods of operation" published Dec. 2, 2021; U.S. Pat. No. 11,173, 311, entitled "Methods for programming an implantable medical device and related systems and devices" issued Nov. 16, 2021; U.S. Patent Publication Number 2021-0020294 entitled "METHODS, DEVICES AND SYSTEMS FOR HOLISTIC INTEGRATED HEALTHCARE PATIENT MANAGEMENT" published Jan. 21, 2021; U.S. Pat. No. 6,622,045, entitled "System and method for remote programming of implantable cardiac stimulation devices" issued Sep. 16, 2003; incorporated by reference herein in their entireties.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference in their entireties. The IMD may monitor transthoracic impedance, such as implemented by the Cor-Vue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference in their entireties. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference in their entireties. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support and/or merely monitor one or more physiologic characteristics of interest (e.g., PAP, CA signals, impedance, heart sounds).

Embodiments herein may be incorporated with the structure and functionality (e.g., detection and analysis of the corresponding types of biological signals and determinations of the corresponding types of non-physiologic conditions) described in any or all of the publications referenced herein, including the following: U.S. patent application Ser. No. 16/930,791, filed Jul. 16, 2020, and titled "METHODS, DEVICES AND SYSTEMS FOR HOLISTIC INTEGRATED HEALTHCARE PATIENT MANAGEMENT"; U.S. Patent Publication Number 2014/0275827, entitled "METHOD AND SYSTEM FOR DERIVING EFFECTIVENESS OF MEDICAL TREATMENT OF A PATIENT" published Sep. 18, 2014; U.S. Patent Publication Number 2014/0039238, entitled "SYSTEMS AND METHODS FOR CONTROLLING NEUROSTIMULATION OF ACUPUNCTURE SITES USING AN IMPLANTABLE CAR- DIAC RHYTHM MANAGEMENT DEVICE" published Feb. 6, 2014; U.S. Patent Publication Number 2013/0204147, entitled "ATRIAL FIBRILLATION DETECTION BASED ON PULMONARY ARTERY PRESSURE DATA" published Aug. 8, 2013; U.S. Patent Publication Number 2013/0116583, entitled "SYSTEMS AND METHODS FOR PREDICTING AND CORROBORATING PULMONARY FLUID OVERLOADS USING AN IMPLANTABLE MEDICAL DEVICE" published May 9, 2013; U.S. Patent Publication Number 2012/0089032, entitled "METHOD AND SYSTEM FOR DISCRIMINATING AND MONITORING ATRIAL ARRHYTHMIA BASED ON CARDIOGENIC IMPEDANCE" published Apr. 12, 2012; U.S. patent application Ser. No. 11/378,604, filed Mar. 16, 2006, of Kroll et al., entitled, "System and Method for Detecting Arterial Blood Pressure based on Aortic Electrical Resistance using an Implantable Medical Device," now U.S. Pat. No. 7,654,964; U.S. Patent Publication Number 2011/0125206, entitled "SINGLE CHAMBER IMPLANTABLE MEDICAL DEVICE FOR CONFIRMING ARRHYTHMIA THROUGH RETROSPECTIVE CARDIAC SIGNALS" published May 26, 2011; U.S. Patent Publication Number 2014/0221771, entitled "METHOD AND IMPLANTABLE SYSTEM FOR BLOOD-GLUCOSE CONCENTRATION MONITORING USING PARALLEL METHODOLOGIES" published Aug. 7, 2014; U.S. Patent Publication Number 2014/0058278, entitled "SYSTEMS AND METHODS FOR DETECTING ISCHEMIC EVENTS" published Feb. 27, 2014; U.S. Patent Publication Number 2013/0218036, entitled "METHODS AND SYSTEMS TO CORRELATE ARRHYTHMIC AND ISCHEMIC EVENTS" published Aug. 22, 2013; U.S. Patent Publication Number 2012/0197149, entitled "SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE" published Aug. 2, 2012; U.S. Patent Publication Number 2012/0065527, entitled "METHODS AND SYSTEMS FOR MONITORING ATRIAL STIFFNESS" published Mar. 15, 2012; U.S. Patent Publication Number 2012/0046528, entitled "SYSTEM AND METHOD FOR DETECTING AND TREATING CARDIOVASCULAR DISEASE" published Feb. 23, 2012; U.S. Patent Publication Number 2011/0004111, entitled "ISCHEMIA DETECTION USING INTRA-CARDIAC SIGNALS" published Jan. 6, 2011; U.S. Pat. No. 8,514,086, entitled "DISPLAYS FOR A MEDICAL DEVICE", issued Aug. 20, 2013; U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFER-ENCE ELECTRODE" issued May 25, 2010; Baj-Rossi et al. "FABRICATION AND PACKAGING OF A FULLY IMPLANTABLE BIOSENSOR ARRAY", (2013) IEEE, pages 166-169. U.S. Pat. No. 6,786,874, entitled "APPARATUS AND METHOD FOR THE COLLECTION OF INTERSTITIAL FLUIDS" issued Sep. 7, 2004; and U.S. Pat. No. 9,872,641, entitled "METHODS, DEVICES AND SYSTEMS RELATED TO ANALYTE MONITORING" issued Jan. 23, 2018; U.S. patent application Ser. No. 11/387,579, filed Mar. 23, 2006, of Koh, entitled "System and Method for Calibrating a Blood Oxygen Saturation Sensor for use with an Implantable Medical Device," now U.S. Pat. No. 8,099,146; U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle," now abandoned; U.S. Patent Publication No. 2005/0215914, to Bornzin et al., entitled "System and Method for Evaluating Heart Failure Based on Ventricular End-Diastolic Volume using an Implantable Medical Device"; U.S. Pat. No. 5,800,467 to Park et al., entitled "Cardio-Synchronous Impedance Measurement System for an Implantable Stimulation Device;" U.S. patent application Ser. No. 11/100,189, filed Apr. 5, 2005, of Koh, entitled "System and Method for Detection of Respiration Patterns via Integration of Intracardiac Electrogram Signals," now U.S. Pat. No. 7,404,799; and in U.S. patent application Ser. No. 11/623,663, filed Jan. 16, 2007, of Zou et al., entitled "Sensor/Lead Systems for use with Implantable Medical Devices," now U.S. Pat. No. 8,388,670, all of which are hereby incorporated by reference in their entireties.

All references, including publications, patent applications and patents, cited herein are hereby incorporated by reference to the same extent as if each reference were individually and specifically indicated to be incorporated by reference and were set forth in its entirety herein.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A healthcare system comprising:
a magnetic resonance (MR) platform comprising:
non-transitory memory configured to store program instructions and patient specific records associated with individual patients, each of the patient specific records including information associated with an implantable medical device (IMD) and a patient; and
one or more processors that, when executing the program instructions, are configured to:
receive a magnetic resonance imaging (MRI) exam referral requesting an MRI exam associated with a first patient specific record from within the patient specific records, the first patient specific record having an associated first IMD and a first patient;
responsive to the MRI exam referral, automatically transmit an MRI exam request alert;

responsive to receiving a response to the MRI exam request alert, provide, via a graphical user interface (GUI) on a display, access to the first patient specific record;
receive MRI settings associated with the first patient specific record, the MRI settings configured to be programmed into the first IMD in advance of the MRI exam; and
responsive to receiving the MRI settings, store the MRI settings in the patient specific record.

2. The healthcare system of claim 1, wherein the MR platform is configured to integrate with i) an existing device platform, ii) a patient application, iii) a third party healthcare management system, or iv) a device-based health kit.

3. The healthcare system of claim 1, wherein responsive to the MRI exam referral, the one or more processors are further configured to automatically generate a ticket associated with the first patient.

4. The healthcare system of claim 1, wherein the one or more processors are further configured to receive a query.

5. The system of claim 1, wherein the memory is further configured to store MRI conditions of use associated with a plurality of IMDs or links to the MRI conditions of use associated with the plurality of IMDs.

6. The system of claim 1, wherein the memory is further configured to store adverse reports associated with a plurality of IMDs or links to the adverse reports associated with the plurality of IMDs.

7. The system of claim 1, wherein the memory is further configured to store a centralized ledger including data associated with a plurality of patients.

8. The system of claim 1, wherein the memory is further configured to store MRI history associated with the first patient specific record, wherein the MRI history includes information associated with one or more previous MRI exams of the first patient.

9. The system of claim 8, wherein the information associated with the one or more previous MRI exams includes i) MR scanner information, ii) MRI scan parameters, or iii) scan regions associated with the one or more previous MRI exams.

10. The system of claim 1, wherein the one or more processors are further configured to, responsive to receiving the MRI exam referral, automatically transmit an MRI scheduling request alert to i) IMD programming personnel, ii) field representative, iii) the first patient, iv) an MRI clinic, v) a physician's office, or vi) an implant clinic.

11. The system of claim 10, wherein the one or more processors are further configured to, in response to receiving a response to the MRI scheduling request alert, provide controlled access to the first patient specific record, wherein the level of control is based on a respondent to the MRI scheduling request alert, wherein the controlled access includes displaying information accessible to the respondent.

12. The system of claim 1, wherein the one or more processors are further configured to:
responsive to receiving the MRI exam referral, automatically transmit an MRI scheduling request alert; and
responsive to receiving a response to the MRI scheduling request alert, display scheduling data associated with the MRI exam request via a portal.

13. The system of claim 1, wherein the one or more processors are further configured to determine Smart MRI settings for programming the first IMD associated with the first patient during an MRI exam, wherein the Smart MRI settings are based on information associated with i) previous MRI exams of the first patient, ii) previous MRI exams of a plurality of patients, iii) medication or medication changes indicated in the first patient specific record, or iv) analysis of IMD data or other data associated with the first patient record that indicates therapy needs, wherein the therapy needs include a) whether A-V conduction condition exists in the first patient, b) sufficient base rate to achieve overdrive pacing, or c) increased pacing output to capture.

14. The system of claim 1, wherein the one or more processors are further configured to:

determine Smart MRI settings for programming the first IMD associated with the first patient during an MRI exam, the Smart MRI settings determined using i) data analytics, ii) artificial intelligence (AI), or iii) machine learning; and store the Smart MRI settings in the first patient specific record.

15. The system of claim 1, wherein the first patient specific record further comprises an associated second IMD or a summary of a second implanted system.

* * * * *